United States Patent
Kothuri et al.

(10) Patent No.: US 9,451,303 B2
(45) Date of Patent: *Sep. 20, 2016

(54) METHOD AND SYSTEM FOR GATHERING AND COMPUTING AN AUDIENCE'S NEUROLOGICALLY-BASED REACTIONS IN A DISTRIBUTED FRAMEWORK INVOLVING REMOTE STORAGE AND COMPUTING

(71) Applicant: The Nielsen Company (US), LLC, New York, NY (US)

(72) Inventors: Ravi Kanth V. Kothuri, Nashua, NH (US); Carl Marci, Boston, MA (US); Brian Levine, Needham, MA (US)

(73) Assignee: The Nielsen Company (US), LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,528

(22) Filed: Feb. 27, 2013

(65) Prior Publication Data
US 2013/0318546 A1 Nov. 28, 2013

Related U.S. Application Data

(63) Continuation-in-part of application No. 13/405,611, filed on Feb. 27, 2012.

(60) Provisional application No. 61/603,521, filed on Feb. 27, 2012.

(51) Int. Cl.
*G06Q 10/00* (2012.01)
*G06Q 30/00* (2012.01)
(Continued)

(52) U.S. Cl.
CPC ............ *H04N 21/24* (2013.01); *A61B 5/16* (2013.01); *G06Q 30/0201* (2013.01);
(Continued)

(58) Field of Classification Search
CPC ............ A61B 5/6897; A61B 5/0002; A61B 5/02405; A61B 5/0476; A61B 5/0533; A61B 5/08; A61B 5/11; A61B 5/16; A61B 5/225; A61B 5/1112; H04N 21/24; H04H 60/33; H04H 60/45; G06Q 30/0201
USPC ......................................................... 705/7.29
See application file for complete search history.

(56) References Cited

U.S. PATENT DOCUMENTS 2,549,836 A 4/1951 McIntyre et al.
3,490,439 A 1/1970 Rolston
(Continued)

FOREIGN PATENT DOCUMENTS

DE 10 2010 005 551 7/2011
DE 10 2010 017 415 12/2011
(Continued)

OTHER PUBLICATIONS

Watching Ads Is Real Science Research Companies Monitor Physiological Reactions to Commercials to Determine Their Effectiveness.: [3 Star Edition] Bruce Horvitz Los Angeles Times. Orlando Sentinel [Orlando, Fla] Sep. 1, 1991: D1.*
(Continued)

*Primary Examiner* — Timothy Padot
(74) *Attorney, Agent, or Firm* — Hanley, Flight & Zimmerman, LLC

(57) ABSTRACT

Systems and methods for measuring biologically and behaviorally based responses to content in targeted demographics and locations by way of remote monitoring. Stimuli may be based on location, target demographics, and combinations thereof.

16 Claims, 3 Drawing Sheets

(51) Int. Cl.
*H04N 21/24* (2011.01)
*A61B 5/16* (2006.01)
*H04H 60/33* (2008.01)
*G06Q 30/02* (2012.01)
*A61B 5/00* (2006.01)
*A61B 5/024* (2006.01)
*A61B 5/0476* (2006.01)
*A61B 5/053* (2006.01)
*A61B 5/08* (2006.01)
*A61B 5/11* (2006.01)
*A61B 5/22* (2006.01)
*H04H 60/45* (2008.01)

(52) U.S. Cl.
CPC ........... *H04H 60/33* (2013.01); *A61B 5/0002* (2013.01); *A61B 5/02405* (2013.01); *A61B 5/0476* (2013.01); *A61B 5/0533* (2013.01); *A61B 5/08* (2013.01); *A61B 5/11* (2013.01); *A61B 5/1112* (2013.01); *A61B 5/225* (2013.01); *A61B 5/6897* (2013.01); *H04H 60/45* (2013.01)

(56) References Cited

U.S. PATENT DOCUMENTS

| | | |
|---|---|---|
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,870,579 A | 9/1989 | Hey .............. 705/7.31 |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,024,235 A | 6/1991 | Ayers |
| 5,038,782 A | 8/1991 | Gevins et al. |
| 5,052,401 A | 10/1991 | Sherwin |
| 5,083,571 A | 1/1992 | Prichep |
| 5,137,027 A | 8/1992 | Rosenfeld |
| 5,243,517 A | 9/1993 | Schmidt et al. ........... 364/419.2 |
| 5,273,037 A | 12/1993 | Itil et al. |
| 5,291,888 A | 3/1994 | Tucker |
| 5,295,491 A | 3/1994 | Gevins |
| 5,339,826 A | 8/1994 | Schmidt et al. |
| 5,345,281 A | 9/1994 | Taboada et al. |
| 5,357,957 A | 10/1994 | Itil et al. |
| 5,392,788 A | 2/1995 | Hudspeth |
| 5,406,956 A | 4/1995 | Farwell |
| 5,436,830 A | 7/1995 | Zaltman ........... 364/419.2 |
| 5,447,166 A | 9/1995 | Gevins |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,617,855 A | 4/1997 | Waletzky et al. |
| 5,649,061 A | 7/1997 | Smyth |
| 5,655,534 A | 8/1997 | Ilmoniemi |
| 5,676,138 A | 10/1997 | Zawilinski |
| 5,676,148 A | 10/1997 | Koo et al. .............. 128/661.01 |
| 5,720,619 A | 2/1998 | Fisslinger |
| 5,724,987 A | 3/1998 | Gevins et al. |
| 5,736,986 A | 4/1998 | Sever, Jr. |
| 5,762,611 A | 6/1998 | Lewis et al. |
| 5,771,897 A | 6/1998 | Zufrin |
| 5,774,591 A | 6/1998 | Black et al. |
| 5,800,351 A | 9/1998 | Mann |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. |
| 5,892,566 A | 4/1999 | Bullwinkel |
| 5,961,332 A | 10/1999 | Joao |
| 5,983,129 A | 11/1999 | Cowan et al. |
| 5,995,868 A | 11/1999 | Dorfmeister et al. |
| 6,001,065 A | 12/1999 | DeVito |
| 6,016,444 A | 1/2000 | John |
| 6,021,346 A | 2/2000 | Ryu et al. |
| 6,052,619 A | 4/2000 | John |
| 6,088,040 A | 7/2000 | Oda et al. |
| 6,099,319 A | 8/2000 | Zaltman et al. |
| 6,117,092 A | 9/2000 | Weinstein et al. |
| 6,120,440 A | 9/2000 | Goknar |
| 6,154,669 A | 11/2000 | Hunter et al. |
| 6,161,030 A | 12/2000 | Levendowski et al. |
| 6,171,239 B1 | 1/2001 | Humphrey |
| 6,175,753 B1 | 1/2001 | Menkes et al. |
| 6,212,502 B1 | 4/2001 | Ball et al. |
| 6,228,038 B1 | 5/2001 | Claessens |
| 6,254,536 B1 | 7/2001 | DeVito |
| 6,259,889 B1 | 7/2001 | LaDue |
| 6,270,466 B1 | 8/2001 | Weinstein et al. |
| 6,286,005 B1 | 9/2001 | Cannon |
| 6,289,234 B1 | 9/2001 | Mueller |
| 6,292,688 B1 * | 9/2001 | Patton ............... A61B 5/16 600/300 |
| 6,299,308 B1 | 10/2001 | Voronka et al. |
| 6,301,493 B1 | 10/2001 | Marro et al. |
| 6,315,569 B1 | 11/2001 | Zaltman ............... 434/236 |
| 6,330,470 B1 | 12/2001 | Tucker et al. |
| 6,334,778 B1 | 1/2002 | Brown |
| 6,349,231 B1 | 2/2002 | Musha |
| 6,358,201 B1 | 3/2002 | Childre et al. ............... 600/300 |
| 6,374,143 B1 | 4/2002 | Berrang et al. |
| 6,422,999 B1 * | 7/2002 | Hill ............... A61B 5/0488 600/300 |
| 6,425,764 B1 | 7/2002 | Lamson |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett et al. ............... 702/19 |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,575,902 B1 | 6/2003 | Burton |
| 6,577,329 B1 | 6/2003 | Flickner et al. |
| 6,585,521 B1 | 7/2003 | Obrador |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,688,890 B2 | 2/2004 | von Buegner |
| 6,699,188 B2 | 3/2004 | Wessel |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopinathan et al. |

(56) References Cited

U.S. PATENT DOCUMENTS

| | | | |
|---|---|---|---|
| 6,792,304 B1 | 9/2004 | Silberstein | |
| 6,842,877 B2 | 1/2005 | Robarts et al. | |
| 6,850,252 B1 | 2/2005 | Hoffberg | 345/716 |
| 6,852,875 B2 | 2/2005 | Prakash | 560/40 |
| 6,888,457 B2 | 5/2005 | Wilkinson et al. | 340/540 |
| 6,904,408 B1 | 6/2005 | McCarthy et al. | |
| 6,950,698 B2 | 9/2005 | Sarkela et al. | |
| 6,993,380 B1 | 1/2006 | Modarres | |
| 7,120,880 B1 | 10/2006 | Dryer et al. | |
| 7,127,283 B2 | 10/2006 | Kageyama | |
| 7,130,673 B2 | 10/2006 | Tolvanen-Laakso et al. | |
| 7,150,715 B2 | 12/2006 | Collura et al. | |
| 7,177,675 B2 | 2/2007 | Suffin et al. | |
| 7,194,186 B1 | 3/2007 | Strub et al. | |
| 7,246,081 B2 | 7/2007 | Hill | |
| 7,340,060 B2 | 3/2008 | Tomkins et al. | |
| 7,383,728 B2 | 6/2008 | Noble et al. | |
| 7,496,400 B2 | 2/2009 | Hoskonen et al. | |
| 7,548,774 B2 | 6/2009 | Kurtz et al. | |
| 7,551,952 B2 | 6/2009 | Gevins et al. | |
| 7,627,880 B2 | 12/2009 | Itakura | |
| 7,630,757 B2 | 12/2009 | Dorfmeister et al. | |
| 7,689,272 B2 | 3/2010 | Farwell | |
| 7,697,979 B2 | 4/2010 | Martinerie et al. | |
| 7,698,238 B2 | 4/2010 | Barletta et al. | |
| 7,716,697 B2 | 5/2010 | Morikawa et al. | |
| 7,729,755 B2 | 6/2010 | Laken | |
| 7,739,140 B2 | 6/2010 | Vinson et al. | |
| 7,742,623 B1 | 6/2010 | Moon et al. | |
| 7,751,878 B1 | 7/2010 | Merkle et al. | |
| 7,797,186 B2 | 9/2010 | Dybus | 705/10 |
| 7,805,009 B2 | 9/2010 | Everett et al. | |
| 7,840,248 B2 | 11/2010 | Fuchs et al. | |
| 7,840,250 B2 | 11/2010 | Tucker | |
| 7,853,122 B2 | 12/2010 | Miura et al. | |
| 7,930,199 B1 | 4/2011 | Hill | |
| 7,942,816 B2 | 5/2011 | Satoh et al. | |
| 8,014,847 B2 | 9/2011 | Shastri et al. | |
| 8,027,518 B2 | 9/2011 | Baker et al. | |
| 8,055,722 B2 | 11/2011 | Hille | |
| 8,069,125 B2 | 11/2011 | Jung et al. | |
| 8,082,215 B2 | 12/2011 | Jung et al. | |
| 8,086,563 B2 | 12/2011 | Jung et al. | |
| 8,103,328 B2 | 1/2012 | Turner et al. | |
| 8,165,916 B2 | 4/2012 | Hoffberg et al. | |
| 8,209,224 B2 * | 6/2012 | Pradeep | G06Q 30/0254 705/14.42 |
| 8,235,725 B1 | 8/2012 | Hill | |
| 8,239,030 B1 | 8/2012 | Hagedorn et al. | |
| 8,255,267 B2 | 8/2012 | Breiter | |
| 8,296,172 B2 | 10/2012 | Marci et al. | 705/7.29 |
| 8,327,395 B2 | 12/2012 | Lee et al. | |
| 8,332,883 B2 | 12/2012 | Lee et al. | |
| 8,335,715 B2 | 12/2012 | Pradeep et al. | |
| 8,386,312 B2 | 2/2013 | Pradeep et al. | |
| 8,386,313 B2 | 2/2013 | Pradeep et al. | |
| 8,392,250 B2 | 3/2013 | Pradeep et al. | |
| 8,392,251 B2 | 3/2013 | Pradeep et al. | |
| 8,392,253 B2 | 3/2013 | Pradeep et al. | |
| 8,392,254 B2 | 3/2013 | Pradeep et al. | |
| 8,392,255 B2 | 3/2013 | Pradeep et al. | |
| 8,396,744 B2 | 3/2013 | Pradeep et al. | |
| 8,473,345 B2 | 6/2013 | Pradeep et al. | |
| 8,494,610 B2 | 7/2013 | Pradeep et al. | |
| 8,494,905 B2 | 7/2013 | Pradeep et al. | |
| 8,533,042 B2 | 9/2013 | Pradeep et al. | |
| 8,548,852 B2 | 10/2013 | Pradeep et al. | |
| 8,600,100 B2 | 12/2013 | Hill | |
| 8,655,428 B2 | 2/2014 | Pradeep et al. | |
| 8,655,437 B2 | 2/2014 | Pradeep et al. | |
| 8,793,715 B1 | 7/2014 | Weitzenfeld et al. | |
| 2001/0013009 A1 | 8/2001 | Greening et al. | 705/10 |
| 2001/0056225 A1 | 12/2001 | DeVito | |
| 2002/0059577 A1 | 5/2002 | Lu et al. | 725/9 |
| 2002/0072952 A1 | 6/2002 | Hamzey et al. | |
| 2002/0077534 A1 | 6/2002 | DuRousseau | |
| 2002/0103429 A1 | 8/2002 | deCharms | |
| 2002/0107454 A1 | 8/2002 | Collura et al. | |
| 2002/0188216 A1 | 12/2002 | Kayyali et al. | |
| 2002/0188217 A1 | 12/2002 | Farwell | |
| 2002/0193670 A1 | 12/2002 | Garfield et al. | |
| 2003/0013981 A1 | 1/2003 | Gevins et al. | |
| 2003/0055355 A1 | 3/2003 | Viertio-Oja | |
| 2003/0059750 A1 | 3/2003 | Bindler et al. | |
| 2003/0063222 A1 | 4/2003 | Creed et al. | 348/687 |
| 2003/0065524 A1 | 4/2003 | Giacchetti et al. | |
| 2003/0066071 A1 | 4/2003 | Gutta et al. | |
| 2003/0067486 A1 | 4/2003 | Lee et al. | |
| 2003/0073921 A1 | 4/2003 | Sohmer et al. | |
| 2003/0081834 A1 | 5/2003 | Philomin et al. | |
| 2003/0093792 A1 | 5/2003 | Labeeb et al. | 725/46 |
| 2003/0100998 A2 | 5/2003 | Brunner et al. | |
| 2003/0149344 A1 | 8/2003 | Nizan | |
| 2003/0165270 A1 | 9/2003 | Endrikhovski et al. | |
| 2003/0208754 A1 | 11/2003 | Sridhar et al. | |
| 2004/0005143 A1 | 1/2004 | Tsuru et al. | |
| 2004/0013398 A1 | 1/2004 | Miura et al. | |
| 2004/0073129 A1 | 4/2004 | Caldwell et al. | |
| 2004/0077934 A1 | 4/2004 | Massad | |
| 2004/0092809 A1 | 5/2004 | DeCharms | |
| 2004/0098298 A1 | 5/2004 | Yin | |
| 2004/0111033 A1 | 6/2004 | Oung et al. | |
| 2004/0133081 A1 | 7/2004 | Teller et al. | 600/300 |
| 2004/0161730 A1 | 8/2004 | Urman | |
| 2004/0187167 A1 | 9/2004 | Maguire et al. | |
| 2004/0193068 A1 | 9/2004 | Burton et al. | |
| 2004/0210159 A1 | 10/2004 | Kibar et al. | |
| 2004/0219184 A1 | 11/2004 | Brown et al. | 424/423 |
| 2004/0220483 A1 | 11/2004 | Yeo et al. | |
| 2005/0010116 A1 | 1/2005 | Korhonen et al. | |
| 2005/0060312 A1 | 3/2005 | Curtiss et al. | 707/7 |
| 2005/0062637 A1 | 3/2005 | El Zabadani et al. | 341/176 |
| 2005/0071462 A1 | 3/2005 | Bodin et al. | 709/224 |
| 2005/0071865 A1 | 3/2005 | Martins | 725/10 |
| 2005/0079474 A1 | 4/2005 | Lowe | |
| 2005/0107716 A1 | 5/2005 | Eaton et al. | |
| 2005/0143629 A1 | 6/2005 | Farwell | |
| 2005/0154290 A1 | 7/2005 | Langleben | |
| 2005/0177058 A1 | 8/2005 | Sobell | |
| 2005/0197590 A1 | 9/2005 | Osorio et al. | |
| 2005/0223237 A1 | 10/2005 | Barletta et al. | |
| 2005/0227233 A1 | 10/2005 | Buxton et al. | |
| 2005/0240956 A1 | 10/2005 | Smith et al. | |
| 2005/0273017 A1 | 12/2005 | Gordon | |
| 2005/0288954 A1 | 12/2005 | McCarthy et al. | |
| 2005/0289582 A1 | 12/2005 | Tavares et al. | |
| 2006/0010470 A1 | 1/2006 | Kurosaki et al. | |
| 2006/0041548 A1 * | 2/2006 | Parsons | G06Q 30/02 |
| 2006/0064037 A1 | 3/2006 | Shalon et al. | |
| 2006/0094970 A1 | 5/2006 | Drew | |
| 2006/0094971 A1 | 5/2006 | Drew | |
| 2006/0111621 A1 | 5/2006 | Coppi et al. | |
| 2006/0111644 A1 | 5/2006 | Guttag et al. | |
| 2006/0129458 A1 | 6/2006 | Maggio | 705/14 |
| 2006/0143647 A1 | 6/2006 | Bill | |
| 2006/0149337 A1 | 7/2006 | John | |
| 2006/0167376 A1 | 7/2006 | Viirre et al. | |
| 2006/0190822 A1 | 8/2006 | Basson et al. | |
| 2006/0217598 A1 | 9/2006 | Miyajima et al. | |
| 2006/0256133 A1 | 11/2006 | Rosenberg | |
| 2006/0257834 A1 | 11/2006 | Lee et al. | |
| 2006/0258926 A1 | 11/2006 | Ali et al. | |
| 2006/0259360 A1 | 11/2006 | Flinn et al. | |
| 2006/0265022 A1 | 11/2006 | John et al. | |
| 2006/0293608 A1 | 12/2006 | Rothman et al. | |
| 2006/0293921 A1 | 12/2006 | McCarthy et al. | |
| 2007/0016096 A1 | 1/2007 | McNabb | |
| 2007/0038516 A1 | 2/2007 | Apple et al. | 705/14 |
| 2007/0048707 A1 | 3/2007 | Caamano et al. | |
| 2007/0055169 A1 | 3/2007 | Lee et al. | |
| 2007/0060830 A1 | 3/2007 | Le et al. | |
| 2007/0060831 A1 | 3/2007 | Le et al. | |
| 2007/0066874 A1 | 3/2007 | Cook | |
| 2007/0066914 A1 | 3/2007 | Le et al. | |

(56) References Cited

U.S. PATENT DOCUMENTS

| | | |
|---|---|---|
| 2007/0066915 A1 | 3/2007 | Frei et al. |
| 2007/0066916 A1 | 3/2007 | Lemos |
| 2007/0106170 A1 | 5/2007 | Dunseath, Jr. et al. |
| 2007/0135727 A1 | 6/2007 | Virtanen et al. |
| 2007/0135728 A1 | 6/2007 | Snyder et al. |
| 2007/0150916 A1 | 6/2007 | Begole et al. |
| 2007/0173733 A1 | 7/2007 | Le et al. |
| 2007/0225585 A1 | 9/2007 | Washbon et al. |
| 2007/0225674 A1 | 9/2007 | Molnar et al. |
| 2007/0235716 A1 | 10/2007 | Delic et al. |
| 2007/0238945 A1 | 10/2007 | Delic et al. |
| 2007/0249952 A1 | 10/2007 | Rubin et al. |
| 2007/0250901 A1 | 10/2007 | McIntire et al. ............. 725/146 |
| 2007/0265507 A1 | 11/2007 | de Lemos |
| 2007/0282566 A1 | 12/2007 | Whitlow et al. |
| 2008/0001600 A1 | 1/2008 | deCharms |
| 2008/0027345 A1 | 1/2008 | Kumada et al. |
| 2008/0039737 A1 | 2/2008 | Breiter et al. |
| 2008/0065468 A1 | 3/2008 | Berg et al. |
| 2008/0081961 A1 | 4/2008 | Westbrook et al. |
| 2008/0082019 A1 | 4/2008 | Ludving et al. |
| 2008/0091512 A1* | 4/2008 | Marci ............... G06Q 30/0242 705/7.29 |
| 2008/0097854 A1 | 4/2008 | Young |
| 2008/0144882 A1 | 6/2008 | Leinbach et al. |
| 2008/0147488 A1 | 6/2008 | Tunick et al. |
| 2008/0147742 A1 | 6/2008 | Allen ......................... 707/104.1 |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030780 A1 | 1/2009 | York et al. ...................... 705/10 |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0112077 A1 | 4/2009 | Nguyen et al. |
| 2009/0112117 A1 | 4/2009 | Rewari |
| 2009/0119154 A1 | 5/2009 | Jung et al. |
| 2009/0131764 A1 | 5/2009 | Lee et al. ....................... 600/301 |
| 2009/0132441 A1 | 5/2009 | Muller et al. |
| 2009/0133047 A1 | 5/2009 | Lee et al. |
| 2009/0150919 A1 | 6/2009 | Lee et al. |
| 2009/0156907 A1 | 6/2009 | Jung et al. |
| 2009/0156955 A1 | 6/2009 | Jung et al. |
| 2009/0158308 A1 | 6/2009 | Weitzenfeld et al. |
| 2009/0163777 A1 | 6/2009 | Jung et al. |
| 2009/0171164 A1 | 7/2009 | Jung et al. |
| 2009/0187467 A1 | 7/2009 | Fang et al. |
| 2009/0195392 A1 | 8/2009 | Zalewski |
| 2009/0214060 A1 | 8/2009 | Chuang et al. |
| 2009/0248496 A1 | 10/2009 | Hueter et al. |
| 2009/0248594 A1 | 10/2009 | Castleman et al. |
| 2009/0253996 A1 | 10/2009 | Lee et al. |
| 2009/0259137 A1 | 10/2009 | Delic et al. |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328016 A1 | 12/2009 | Pradeep et al. |
| 2010/0004977 A1 | 1/2010 | Marci et al. ...................... 705/10 |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0076333 A9 | 3/2010 | Burton et al. |
| 2010/0094702 A1 | 4/2010 | Silberstein |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0153175 A1 | 6/2010 | Pearson et al. |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0211439 A1 | 8/2010 | Marci et al. |
| 2010/0214318 A1 | 8/2010 | Pradeep et al. |
| 2010/0215289 A1 | 8/2010 | Pradeep et al. |
| 2010/0223094 A1 | 9/2010 | Cumming et al. |
| 2010/0234752 A1 | 9/2010 | Sullivan et al. |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0274152 A1 | 10/2010 | McPeck et al. |
| 2010/0274153 A1 | 10/2010 | Tucker et al. |
| 2010/0317988 A1 | 12/2010 | Terada et al. |
| 2010/0323716 A1 | 12/2010 | Jaffri |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0040202 A1 | 2/2011 | Luo et al. |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0084795 A1 | 4/2011 | Fukuyori |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0144519 A1 | 6/2011 | Causevic |
| 2011/0161163 A1 | 6/2011 | Carlson et al. |
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0256520 A1 | 10/2011 | Siefert |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |

(56) References Cited

U.S. PATENT DOCUMENTS

| | | | |
|---|---|---|---|
| 2011/0282749 A1 | 11/2011 | Pradeep et al. | |
| 2011/0298706 A1 | 12/2011 | Mann | |
| 2011/0301431 A1 | 12/2011 | Greicius et al. | |
| 2011/0319975 A1 | 12/2011 | Ho et al. | |
| 2012/0002848 A1 | 1/2012 | Hill | |
| 2012/0022391 A1 | 1/2012 | Leuthardt | |
| 2012/0036004 A1 | 2/2012 | Pradeep et al. | |
| 2012/0036005 A1 | 2/2012 | Pradeep et al. | |
| 2012/0046993 A1 | 2/2012 | Hill | |
| 2012/0054018 A1 | 3/2012 | Pradeep et al. | |
| 2012/0072289 A1 | 3/2012 | Pradeep et al. | |
| 2012/0072939 A1* | 3/2012 | Crenshaw | H04H 60/33 725/12 |
| 2012/0089552 A1 | 4/2012 | Chang et al. | |
| 2012/0108995 A1 | 5/2012 | Pradeep et al. | |
| 2012/0130800 A1 | 5/2012 | Pradeep et al. | |
| 2012/0203640 A1 | 8/2012 | Karmarkar | |
| 2012/0249797 A1 | 10/2012 | Haddick et al. | |
| 2012/0254909 A1 | 10/2012 | Serdiuk | |
| 2012/0289794 A1 | 11/2012 | Jain et al. | |
| 2013/0024272 A1 | 1/2013 | Pradeep et al. | |
| 2013/0060125 A1 | 3/2013 | Zeman et al. | |
| 2013/0094722 A1 | 4/2013 | Hill | |
| 2013/0121591 A1 | 5/2013 | Hill | |
| 2013/0166373 A1 | 6/2013 | Pradeep et al. | |
| 2013/0185140 A1 | 7/2013 | Pradeep et al. | |
| 2013/0185141 A1 | 7/2013 | Pradeep et al. | |
| 2013/0185142 A1 | 7/2013 | Pradeep et al. | |
| 2013/0185144 A1 | 7/2013 | Pradeep et al. | |
| 2013/0185145 A1 | 7/2013 | Pradeep et al. | |
| 2013/0304540 A1 | 11/2013 | Pradeep et al. | |
| 2013/0311132 A1 | 11/2013 | Tobita | |
| 2013/0332259 A1 | 12/2013 | Pradeep et al. | |
| 2014/0025620 A1 | 1/2014 | Greenzeiger et al. | |
| 2014/0039857 A1 | 2/2014 | Hill | |
| 2014/0039975 A1 | 2/2014 | Hill | |
| 2014/0162225 A1 | 6/2014 | Hill | |

FOREIGN PATENT DOCUMENTS

| | | |
|---|---|---|
| GB | 1374658 | 11/1974 |
| GB | 2221759 | 2/1990 |
| JP | 05/293172 | 11/1993 |
| JP | 2001-147944 | 5/2001 |
| JP | 2002/000577 | 1/2002 |
| JP | 2002056500 | 2/2002 |
| JP | 2002/344904 | 11/2002 |
| JP | 2003/111106 | 4/2003 |
| JP | 2003/178078 | 6/2003 |
| JP | 2003522580 | 7/2003 |
| JP | 2005-51654 | 2/2005 |
| JP | 2006-227994 | 8/2006 |
| JP | 2006/323547 | 11/2006 |
| JP | 2006-6355 | 7/2007 |
| WO | 95/18565 | 7/1995 |
| WO | 97/17774 | 5/1997 |
| WO | 97/40745 | 11/1997 |
| WO | 97/41673 | 11/1997 |
| WO | 00/17827 | 3/2000 |
| WO | 02/100241 | 12/2002 |
| WO | 02/102238 | 12/2002 |
| WO | 2004/100765 | 11/2004 |
| WO | 2006/005767 | 1/2006 |
| WO | 2007/019584 | 2/2007 |
| WO | 2008/077178 | 7/2008 |
| WO | 2008/109694 | 9/2008 |
| WO | 2008/109699 | 9/2008 |
| WO | 2008/121651 | 10/2008 |
| WO | 2008/137579 | 11/2008 |
| WO | 2008/154410 | 12/2008 |
| WO | 2009/018374 | 2/2009 |
| WO | 2009/052833 | 4/2009 |
| WO | 2011/055291 | 5/2011 |
| WO | 2011/056679 | 5/2011 |
| WO | 2011/062795 | 5/2011 |

OTHER PUBLICATIONS

Multi-Platform Messaging: The Medium Matters. Treutler, Theresa; Levine, Brian; Marci, Carl D. Journal of Advertising Research50.3 (2010): 243.*
The Emotional Quotient of Soup Shopping. Iian Brat. The Wall Street Journal. Feb. 17, 2010, p. B6.*
One to One Interactive and Innerscope Research Release Preliminary Biomeasures Study Results; Initial Findings Suggest Biomeasures Able to Predict Online Community's Rating of Viral Video Content. PR Newswire [New York] Feb. 28, 2007: n/a.*
U.S. Appl. No. 12/749,376, filed Mar. 29, 2010.
U.S. Appl. No. 12/426,259, filed Apr. 19, 2009.
U.S. Appl. No. 13/089,752, filed Apr. 19, 2011.
International Search Report dated Mar. 24, 2008 of International Patent Application No. PCT/US2007/019398.
International Search Report dated Nov. 9, 2010 of International Patent Application No. PCT/US2010/031375.
International Search Report dated Oct. 21, 2010 of International Patent Application No. PCT/US2010/029162.
International Search Report dated Nov. 22, 2011 of International Patent Application No. PCT/US2011/033050.
Non-Final Office Action dated Oct. 18, 2010 of related U.S. Appl. No. 11/850,650.
Final Office Action dated Jun. 8, 2011 of related U.S. Appl. No. 11/850,650.
Non-Final Office Action dated Dec. 13, 2011 of related U.S. Appl. No. 11/850,650.
Notice of Allowance dated Jul. 16, 2012 of related U.S. Appl. No. 11/850,650.
Non-Final Office Action dated Dec. 21, 2011 of related U.S. Appl. No. 12/749,376.
Final Office Action dated Oct. 4, 2012 of related U.S. Appl. No. 12/749,376.
Non-Final Office Action dated Apr. 1, 2013 of related U.S. Appl. No. 12/749,376.
Non-Final Office Action dated Apr. 25, 2012 of related U.S. Appl. No. 12/426,259.
Final Office Action dated Dec. 19, 2012 of related U.S. Appl. No. 12/426,259.
Non-Final Office Action dated Feb. 21, 2013 of related U.S. Appl. No. 13/657,432.
Non-Final Office Action dated Feb. 13, 2013 of related U.S. Appl. No. 13/089,752.
Australian Office Action dated Mar. 26, 2012 or corresponding Australian Patent Application No. 2007293092.
European Office Action dated Nov. 11, 2011 of corresponding European Patent Application No. 10717912.9.
European Supplementary Search Report dated Mar. 1, 2013 of corresponding European Patent Application No. 10717912.9.
European Office Action dated Mar. 14, 2013 of corresponding European Patent Application No. 10717912.9.
European Office Action dated Nov. 29, 2011 of corresponding European Patent Application No. 10717932.7.
Japanese Office Action dated Apr. 23, 2012 of corresponding Japanese Patent Application No. 2009-527401.
Canadian Office Action dated Jul. 24, 2014 of related Canadian Patent Application No. 2,662,632.
"ARF, AAAA and ANA Are Getting Emotional about Engagement", Presentation, pp. 1-103 (2005).
Boltz, M.G., "The cognitive processing of film and musical soundtracks", *Memory & Cognition*, 32(7):1194-1205 (2004).
Christie et al., "Autonomic specificity of discrete emotion and dimensions of affective space: a multivariate approach", *Int'l J. Psychophysiol.*, 51:143-153 (2004).
Coombes et al., "Emotion and movement: Activation of defensive circuitry alters the magnitude of a sustained muscle contraction", *Neurosci. Lett.*, 396:192-196 (2006).
Cryer et al., "Pull the plug on stress", *Harv. Bus. Rev.*, 81(7):102-107 (2003).

(56) References Cited

OTHER PUBLICATIONS

Demaree et al., "Predicting facial valence to negative stimuli from resting RSA: Not a function of active emotion regulation", *Cognition and Emotion*, 20(2):161-176 (2006).
Ekman et al., "Autonomic Nervous System Activity Distinguishes among Emotions", *Science*, 221(4616):1208-1210 (1983).
Elton, C., "Measuring emotion at the symphony", http://www.boston.com, pp. 1-3 (2006).
Goldberg, C., "Getting wired could help predict emotions", http://www.boston.com, pp. 1-4 (2005).
Gomez et al., "Respiratory responses associated with affective processing of film stimuli", Biol. Psychol., 68:223-235 (2005).
Hall, B.F., "A New Approach to Measuring Advertising Effectiveness", Article 1502a:1-17 (2001).
Hall, B.F., "Advertising as a Factor of production", *Admap*, pp. 30-32 (2003).
Hall, B.F., "Is cognitive processing the right dimension", *Admap*, pp. 37-39 (2003).
Hall, B.F., "On Measuring the Power of Communications", *JAR*, pp. 1-11 (2004).
Hall, B.F., "Research and strategy: a fall from grace", *Admap*, pp. 2-4 (2003).
Hall, B.F., "Review of Casting for Big Ideas, by Andrew Jaffe", pp. 1-2 (2003).
Hall, B.F., "Why Advertisers Do It", pp. 1-5 (2003).
Hubert, et al., "Autonomic, neuroendocrine, and subjective responses to emotion-inducing film stimuli", *Int'l J. Psychophysiol.*, 11:131-140 (1991).
Levenson et al., "Emotion and Autonomic Nervous System Activity in the Minangkabau of West Sumatra", *J. Personality Soc. Psychol.*, 62(6):972-988 (1992).
Marci et al., "The Effect of Emotional Distance on Pyschophysiologic Concordance and Perceived Empathy Between Patient and Interviewer", *Appl. Psychophysiol. Biofeedback*, 31:115-129 (2006).
McCraty et al., "Analysis of twenty-four hour heart rate variability in patients with panic disorder", Biol. Psychol., 56(2):131-150 (2001).
McCraty et al., "Electrophysiolocial Evidence of Intuition: Part 1. The Surprising Role of the Heart", J. Altern. Complement. Med., 10(1):133-143 (2004).
McCraty et al., "Electrophysiological Evidence of Intuition: Part 2. A System-Wide Process?", J. Altern. Complement. Med., 10(2\0):325-336 (2004).
McCraty et al., "Impact of a Workplace Stress Reduction Program on Blood Pressure and Emotional Health in Hypertensive Employees", *J. Altern. Complement. Med.*, 9(3):355-369 (2003).
McCraty et al., "The Effects of Different Types of Music on Mood, Tension, and Mental Clarity", *Altern. Ther. Health Med.*, 4(1):75-84 (1998).
McCraty et al., "The Effects of Emotions on Short-Term Power Spectrum Analysis of Heart RateVariability", *Am. J. Cardiol.*, 76(14):1089-1093 (1995).
McCraty et al., "The Impact of a New Emotional Self-Management Program on Stress, Emotions, Heart Rate Variability, DHEA and Cortisol", *Intergr. Physiol. Behav. Sci.*, 33(2):151-170 (1998).
McCraty et al., "The Impact of an Emotional Self-Management Skills Course on Psychosocial Functioning and Autonomic Recovery to Stress in Middle School Children", Integr. Physiol. Behav. Sci., 34(4):246-268 (1999).
Melillo, W., "Inside the consumer mind: What Neuroscience can tell us about marketing", http://www.answerstream.com, pp. 1-13 (2006).
Miller et al., "Influence of Specific Emotional States on Autonomic Reactivity and Pulmonary Function in Asthmatic Children", *J. Am. Acad. Child Adolescent Psychiatry*, 36(5):669-677 (1997).
Murphy et al., "The Heart Reinnervates After Transplantation", *Ann. Thorac. Surg.*, 69(6):1769-1781 (2000).
Ranii, D., "Adding Science to Gut Check", *The News & Observer*, pp. 1 (2005).

Rosenberg, K., "Emotional R.O.I.", *The Hub*, pp. 24-25 (2006).
Tiller et al., "Cardiac Coherence: A New, Noninvasive Measure of Autonomic Nervous System Order", *Altern. Ther. Health Med.*, 2(1):52-65 (1996).
"Topline: Emotional Response to Advertising", *MSW Research*, pp. 1-6 (2005).
Umetani et al., "Twenty-Four Hour Time Domain Heart Rate Variability and Heart Rate: Relations to Age and Gender Over Nine Decades", *J. Am. Coll. Cardiol.*, 31(3):593-601 (1998).
Von Leupoldt et al., "Emotions in a Body Plethysmograph", *J. Psychophysiol.*, 18(4):170-176 (2004).
Wearable feedback systems for rehabilitation Sung, Michael; Marci, Carl; Pentland, Alex. Journal of NeuroEngineering and Rehabilitation 2 (2005), 2 pgs.
Aaker et al., "Warmth in Advertising: Measurement, Impact, and Sequence Effects," Journal of Consumer Research, vol. 12, No. 4, pp. 365-381, (Mar. 1986), 18 pages.
Akam, et al., "Oscillations and Filtering Networks Support Flexible Routing of Information," Neuron, vol. 67, pp. 308-320, Elsevier, (Jul. 29, 2010), 13 pages.
Allen et al., "A Method of Removing Imaging Artifact from Continuous EEG Recorded during Functional MRI," Neuroimage, vol. 12, 230-239, (Aug. 2000), 12 pages.
Ambler et al., "Ads on the Brain: A Neuro-Imaging Comparison of Cognitive and Affective Advertising Stimuli," London Business School, Centre for Marketing Working Paper, No. 00-902, (Mar. 2000), 23 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Arousal in Sport, in Encyclopedia of Applied Psychology, vol. 1, p. 159, retrieved from Google Books, (Spielberger, ed., Elsevier Academic Press, 2004), 1 page.
Badre, et al. "Frontal Cortex and the Discovery of Abstract Action Rules," Neuron, vol. 66, pp. 315-326, Elsevier, (Apr. 29, 2010), 12 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal modulation of visual processing in humans," Nature Neuroscience, vol. 3, No. 4, Nature America, http//neurosci.nature.com, (Apr. 2000), 5 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Belch et al., "Psychophysiological and Cognitive Response to Sex in Advertising," Advances in Consumer Research, vol. 9, pp. 424-427, (1982), 6 pages.
Bimler et al., "Categorical perception of facial expressions of emotion: Evidence from multidimensional scaling," Cognition and Emotion, vol. 15(5), pp. 633-658 (Sep. 2001), 26 pages.
Blakeslee, "If You Have a 'Buy Button' in Your Brain, What Pushes It?" The New York Times, www.nytimes.com, (Oct. 19, 2004), 3 pages.
Braeutigam, "Neuroeconomics-From neural systems to economic behavior," Brain Research Bulletin, vol. 67, pp. 355-360, Elsevier, (2005), 6 pages.
Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.
Buschman, et al., "Top-Down Versus Bottom-Up Control of Attention in the Prefrontal and Posterior Parietal Cortices," Science, vol. 315, www.sciencemag.org/cgi/content/full/315/5820/1860, American Association for the Advancement of Science, (Mar. 30, 2007), 4 pages.
Buzsaki, "Neural Syntax: Cell Assemblies, Synapsembles, and Readers," Neuron, vol. 68, Elsevier, (Nov. 4, 2010), 24 pages.
Canolty, et al., "High Gamma Power Is Phase-Locked to Theta Oscillations in Human Neocortex," Science, vol. 313, www.sciencemag.org, (Sep. 15, 2006), 3 pages.

(56) References Cited

OTHER PUBLICATIONS

Canolty, et al., "The functional role of cross-frequency coupling," Trends in Cognitive Sciences, Elsevier, (Nov. 2010) 11 pages.
Chang, et al., "Categorical speech representation in human superior temporal gyrus," Nature Neuroscience, doi: 10.1038/nn.2641, (Oct. 3, 2010), 6 pages.
Cheng, et al. "Gender Differences in the Mu Rhythm of the Human Mirror-Neuron System," PLos ONE, vol. 3, Issue 5, www.plosone.org, (May 2008), 7 pages.
Coan, J. A, et al., "Voluntary Facial Expression and Hemispheric Asymmetry Over the Frontal Cortex," Psychophysiology, 38 (Nov. 2001), pp. 912-925, 14 pages.
Cohn et al., "Active Learning with Statistical Models," Journal of Artificial Intelligence Research 4, AI Access Foundation and Morgan Kaufmann Publishers, USA, 1996, 17 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.
D'Esposito, "From cognitive to neural models of working memory," Phil. Trans. R. Soc. B, doi: 10.1098/rstb.2007.2086, (Mar. 30, 2007), 12 pages.
Davidson, et al., "The functional neuroanatomy of emotion and affective style," Trends in Cognitive Sciences, vol. 3, No. 1, (Jan. 1999), 11 pages.
de Gelder et al., "Categorical Perception of Facial Expressions: Categories and their Internal Structure," Cognition and Emotion, vol. 11(1), pp. 1-23 (1997), 23 pages.
Desmet, "Measuring Emotions: Development and Application of an Instrument to Measure Emotional Responses to Products," to be published in Funology: From Usability to Enjoyment, Kluwer Academic Publishers, (Blythe et al., eds., 2004), 13 pages.
Dien, et al., "Application of Repeated Measures ANOVA to High-Density ERP Datasets: A Review and Tutorial," in Event-Related Potentials: A Methods Handbook pp. 57-82, (Todd C. Handy, ed., 2005), 14 pages.
Edgar, et al., "Digital Filters in ERP Research," in Event-Related Potentials: A Methods Handbook pp. 85-113, (Todd C. Handy, ed., 2005), 15 pages.
EEG Protocols, "Protocols for EEG Recording," retrieved from the Internet on Aug. 23, 2011, http://www.q-metrx.com/EEGrecordingProtocols.pdf, (Nov. 13, 2007), 3 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.
European Office Action dated Nov. 29, 2011 of corresponding European Patent Application No. 10717932.7, 2 pages.
Filler, "MR Neurography and Diffusion Tensor Imaging: Origins, History & Clinical Impact of the first 50,000 Cases With an Assortment of Efficacy and Utility in a Prospective 5,000 Patient Study Group," Institute for Nerve Medicine, (Nov. 7, 2008), 56 pages.
Final Office Action dated Feb. 27, 2015 of related U.S. Appl. No. 13/779,528, 14 pages.
Final Office Action dated Sep. 24, 2015 of related U.S. Appl. No. 12/426,259, 27 pages.
Flinker, A. et al, "Sub-centimeter language organization in the human temporal lobe," Brain and Language, Elsevier Inc., (2010), doi.org/10.1016/j.bandl.2010.09.009, 7 pages.
Fogelson, et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.
Friedman, et al., "Event-Related Potential (ERP) Studies of Memory Encoding and Retrieval: A Selective Review," Microscopy Research and Technique 51:6-28, Wiley-Less, Inc. (2000), 23 pages.
Fries, "A mechanism for cognitive dynamics: neuronal communication through neuronal coherence," Trends in Cognitive Sciences, vol. 9, No. 10, pp. 474-480, Elsevier B.V. www.sciencedirect.com, (Oct. 2005), 7 pages.
Fuster, "Cortex and Memory: Emergence of a New Paradigm," Journal of Cognitive Neuroscience, vol. 21, No. 11, pp. 2047-2072, Massachusetts Institute of Technology, (Nov. 2009), 26 pages.
Gaillard, "Problems and Paradigms in ERP Research," Biological Psychology, Elsevier Science Publisher B.V. (1988), 10 pages.
Gargiulo et al., "A Mobile EEG System With Dry Electrodes," (Nov. 2008), 4 pages.
Gazzaley et al., "Top-down Enhancement and Suppression of the Magnitude and Speed of Neural Activity," Journal of Cognitive Neuroscience, vol. 17, No. 3, pp. 507-517, Massachusetts Institute of Technology, (2005), 11 pages.
Grefenstette et al., "Validating the Coverage of Lexical Resources for Affect Analysis and Automatically Classifying New Words along Semantic Axes," Chapter X, 3, Mar. 2004, 16 pages.
Griss et al., "Characterization of micromachined spiked biopotential electrodes", Biomedical Engineering, IEEE Transactions, vol. 49, No. 6, (Jun. 2002), 8 pages.
Haq, "This Is Your Brain on Advertising," BusinessWeek, Market Research, (Oct. 8, 2007), 4 pages.
Hartikainen et al., Manuscript Draft of "Emotionally arousing stimuli compete with attention to left hemispace," NeuroReport, (Sep. 8, 2007), 26 pages.
Hazlett, et al., "Emotional Response to Television Commercials: Facial EMG vs. Self-Report," Journal of Advertising Research, (Apr. 1999), 17 pages.
Herrmann, et al., "Mechanisms of human attention: event-related potentials and oscillations," Neuroscience and Biobehavioral Reviews, pp. 465-476, Elsevier Science Ltd., www.elsevier.com/locate/neubiorev, (2001), 12 pages.
Hopf, et al., "Neural Sources of Focused Attention in Visual Search," Cerebral Cortex, 10:1233-1241, Oxford University Press, (Dec. 2000), 9 pages.
Japanese Office Action dated Apr. 25, 2012 of corresponding Japanese Patent Application No. 2009-527401, 16 pages.
Jung et al., "Analysis and Visualization of Single-Trial Event-Related Potentials," Human Brain Mapping vol. 14, 166-185 (2001), 20 pages.
Kay et al., "Identifying natural images from human brain activity," Nature, vol. 452, pp. 352-356, Nature Publishing Group, (Mar. 20, 2008), 5 pages.
Keren, et al., "Saccadic spike potentials in gamma-band EEG: Characterization, detection and suppression," NeuroImage, http://dx.doi:10.1016/j.neuroimage.2009.10.057, (Oct. 2009), 16 pages.
Kishiyama, et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Kishiyama, et al., "Socioeconomic Disparities Affect Prefrontal Function in Children," Journal of Cognitive Neuroscience pp. 1106-1115, Massachusetts Institute of Technology, (2008), 10 pages.
Klimesch, "EEG alpha and theta oscillations reflect cognitive and memory performance a review and analysis," Brain Research Reviews, vol. 29, 169-195, (1999), 27 pages.
Klimesch, et al., "Episodic and semantic memory: an analysis in the EEG theta and alpha band," Electroencephalography and clinical Neurophysiology, vol. 91, 1994, 14 pages.
Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.
Knight, "Contribution of human hippocampal region to novelty detection," Nature, vol. 383, www.nature.com, (Sep. 19, 1996), 4 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.

(56) References Cited

OTHER PUBLICATIONS

Knight, et al., "Prefrontal cortex regulates inhibition and excitation in distributed neural networks," Acta Psychologica vol. 101, pp. 159-178, Elsevier (1999), 20 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, 3-9 (Feb. 1971), 7 pages.
Lachaux et al., "Measuring Phase Synchrony in Brain Signals," Human Brain Mapping 8 (1999), 194-208, 15 pages.
Lee et al., "What is 'neuromarketing'? A discussion and agenda for future research," International Journal of Psychophysiology, vol. 63, pp. 199-204, Elsevier (2006), 6 pages.
Lekakos, "Personalized Advertising Services Through Hybrid Recommendation Methods: The Case of Digital Interactive Television," Department of Informatics, Cyprus University, (2004), 11 pages.
Lewis et al., "Market Researchers make Increasing use of Brain Imaging," ACNR, vol. 5, No. 3, pp. 36-37, (Jul./Aug. 2005), 2 pages.
Luck, et al., "The speed of visual attention in schizophrenia: Electrophysiological and behavioral evidence," Schizophrenia Research, pp. 174-195, Elsevier B.V. www.sciencedirect.com, (2006), 22 pages.
Makeig, et al., "Dynamic Brain Sources of Visual Evoked Responses," Science, vol. 295, www.sciencemag.org, (Jan. 25, 2002), 5 pages.
Makeig, et al., "Mining event-related brain dynamics," TRENDS in Cognitive Sciences, vol. 8, No. 5, (May 2004), www.sciencedirect.com, 7 pages.
Miltner, et al., "Coherence of gamma-band EEG activity as a basis for associative learning," Nature, vol. 397, www.nature.com, (Feb. 4, 1999), 3 pages.
Moran, et al. "Peak frequency in the theta and alpha bands correlates with human working memory capacity," frontiers in Human Neuroscience, vol. 4, Article 200, www.frontiersin.org, (Nov. 11, 2010), 12 pages.
Neurofocus—Neuroscientific Analysis for Audience Engagement, accessed on Jan. 8, 2010 at http://web.archive.org/web/20080621114525/www.neurofocus.com/BrandImage.htm, (2008), 2 pages.
Newell et al., "Categorical perception of familiar objects," Cognition, vol. 85, Issue 2, pp. 113-143 (Sep. 2002), 31 pages.
Nielsen, "Neuroinformatics in Functional Neuroimaging," Informatics and Mathematical Modeling, Technical University of Denmark, (Aug. 30, 2002), 241 pages.
Non-Final Office Action dated Aug. 1, 2014 of related U.S. Appl. No. 13/779,528, 38 pages.
Oberman et al., "EEG evidence for mirror neuron activity during the observation of human and robot actions: Toward an analysis of the human qualities of interactive robots," Neurocomputing 70 (2007) 2194-2203, 10 pages.
Padgett et al., "Categorical Perception in Facial Emotion Classification," In Proceedings of the 18th Annual Conference of the Cognitive Science Society, pp. 249-253 (1996), 5 pages.
Page et al., "Cognitive Neuroscience, Marketing and Research," Congress 2006—Foresight—The Predictive Power of Research Conference Papers, ESOMAR Publications, (Sep. 17, 2006), 25 pages.
Paller, et al., "Validating neural correlates of familiarity," TRENDS in Cognitive Sciences, vol. 11, No. 6, www.sciencedirect.com, (May 2, 2007), 8 pages.
Palva et al., "Phase Synchrony Among Neuronal Oscillations in the Human Cortex," Journal of Neuroscience 25 (2005), 3962-3972, 11 pages.
Picton, et al., "Guidelines for using human event-related potentials to study cognition: Recording standards and publication criteria," Psychophysiology, pp. 127-152, Society for Psychophysiological Research, (2000), 26 pages.
Rizzolatti et al., "The Mirror-Neuron System," Annu. Rev. Neurosci., vol. 27, pp. 169-192, (Mar. 5, 2004), 30 pages.
Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Rugg, et al., "Event-related potentials and recognition memory," TRENDS in Cognitive Sciences, vol. 11, No. 6, www.sciencedirect.com, (May 3, 2007), 7 pages.
Rugg, et al., "The ERP and cognitive psychology: conceptual issues," (Sep. 1996), 7 pages.
Sammler et al., "Music and emotion: Electrophysiological correlates of the processing of pleasant and unpleasant music," Psychophysiology, vol. 44, Blackwell Publishing Inc., 2007, 12 pages.
Schmidt et al., "Frontal brain electrical activity (EEG) distinguishes valence and intensity of musical emotions," Cognition and Emotion, vol. 15 (4), Psychology Press Ltd, 2001, 14 pages.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Soderlund et al., "Customer Satisfaction and Links to Customer Profitability: An Empirical Examination of the Association Between Attitudes and Behavior," SSE/EFI Working Paper Series in Business Administration, Jan. 1999, 22 pages.
Spencer, "Averaging, Detection, and Classification of Single-Trial ERPs," in Event-Related Potentials: A Methods Handbook, pp. 209-227, (Todd C. Handy, ed., 2005), 10 pages.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, (May 18, 2008), 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri, et al., "A dry electrode for EEG recording," Electroencephalography and clinical Neurophysiology, pp. 376-383, Elsevier Science Ireland Ltd. (1994), 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
U.S. Appl. No. 12/426,259, filed Apr. 19, 2009, 91 pages.
Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
Voytek, et al., "Dynamic Neuroplasticity after Human Prefrontal Cortex Damage," Neuron 68, pp. 401-408, Elsevier Inc., (Nov. 4, 2010), 8 pages.
Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.
Voytek, et al., "Prefrontal cortex and basal ganglia contributions to visual working memory," PNAS Early Edition, www.pnas.org/cgi/doi/10.1073/pnas.1007277107, (2010), 6 pages.
Voytek, et al., "Shifts in gamma phase-amplitude coupling frequency from theta to alpha over posterior cortex during visual tasks," Frontiers in Human Neuroscience, doi: 10.3389/fnhum.2010.00191, (Oct. 19, 2010), 9 pages.
Wang, "Neurophysiological and Computational Principles of Cortical Rhythms in Cognition," Physiol Rev 90: pp. 1195-1268, American Physiological Society, www.prv.org, (2010), 75 pages.

(56) References Cited

OTHER PUBLICATIONS

Waldorff, "Distortion of ERP averages due to overlap from temporally adjacent ERPs: Analysis and correction," Psychophysiology, Society for Psychophysiological Research, Cambridge University Press (1993), 22 pages.
Woodman, et al., "Serial Deployment of Attention During Visual Search," Journal of Experimental Psychology: Human Perception and Performance, vol. 29, No. 1, pp. 121-138, American Physiological Association (2003), 18 pages.
Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.
Yap et al., "TIMER: Tensor Image Morphing for Elastic Registration," NeuroImage, vol. 47, (May 3, 2009), 15 pages.
Yuval-Greenberg, et al., "Transient Induced Gamma-Band Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 9 pages.
Zyga, "A Baseball Cap That Reads Your Mind," PhysOrg.com, located at www.physorg.com/news130152277.html, (May 16, 2008), 11 pages.
Berry, Michael J.A. and Linoff, Gordon S., Data Mining Techniques: For Marketing, Sales, and Customer Relationship Management, John Wiley & Sons, Inc., 1997, 672 pages.
Han, Jiawei and Micheline Kamber Jiawei, Data Mining: Concepts and Techniques, Second Edition (The Morgan Kaufmann Series in Data Management Systems), Elsevier, Inc., 2006, 772 pages.
Liu, Bing, Web Data Mining: Exploring Hyperlinks, Contents, and Usage Data (Data-Centric Systems and Applications), Springer-Verlag, 2007, 643 pages.
Larose, Daniel T., Data Mining Methods and Models, John Wiley & Sons, Inc., 2006, 14 pages.
Notice of Allowance dated Nov. 11, 2015 of related U.S. Appl. No. 13/405,611, 11 pages.
Non-Final Office Action dated Oct. 18, 2010 of related U.S. Appl. No. 11/850,650, 9 pages.
Final Office Action dated Jun. 8, 2011 of related U.S. Appl. No. 11/850,650, 27 pages.
Non-Final Office Action dated Dec. 13, 2011 of related U.S. Appl. No. 11/850,650, 12 pages.
Notice of Allowance dated Jul. 16, 2012 of related U.S. Appl. No. 11/850,650, 9 pages.
Non-Final Office Action dated Oct. 18, 2010 of related U.S. Appl. No. 13/405,611, 20 pages.
Final Office Action dated Feb. 27, 2015 of related U.S. Appl. No. 13/405,611, 26 pages.
Notice of Allowance dated Jul. 7, 2015 of related U.S. Appl. No. 13/405,611, 11 pages.
Canadian Office Action dated Jul. 24, 2014 of corresponding Canadian Patent Application No. 2,662,632, 3 pages.
Supplementary European Search Report dated Mar. 1, 2013 of corresponding European Patent Application No. 10717912.9, 2 pages.
European Office Action dated Mar. 14, 2013 of corresponding European Patent Application No. 10717912.9, 20 pages.

\* cited by examiner

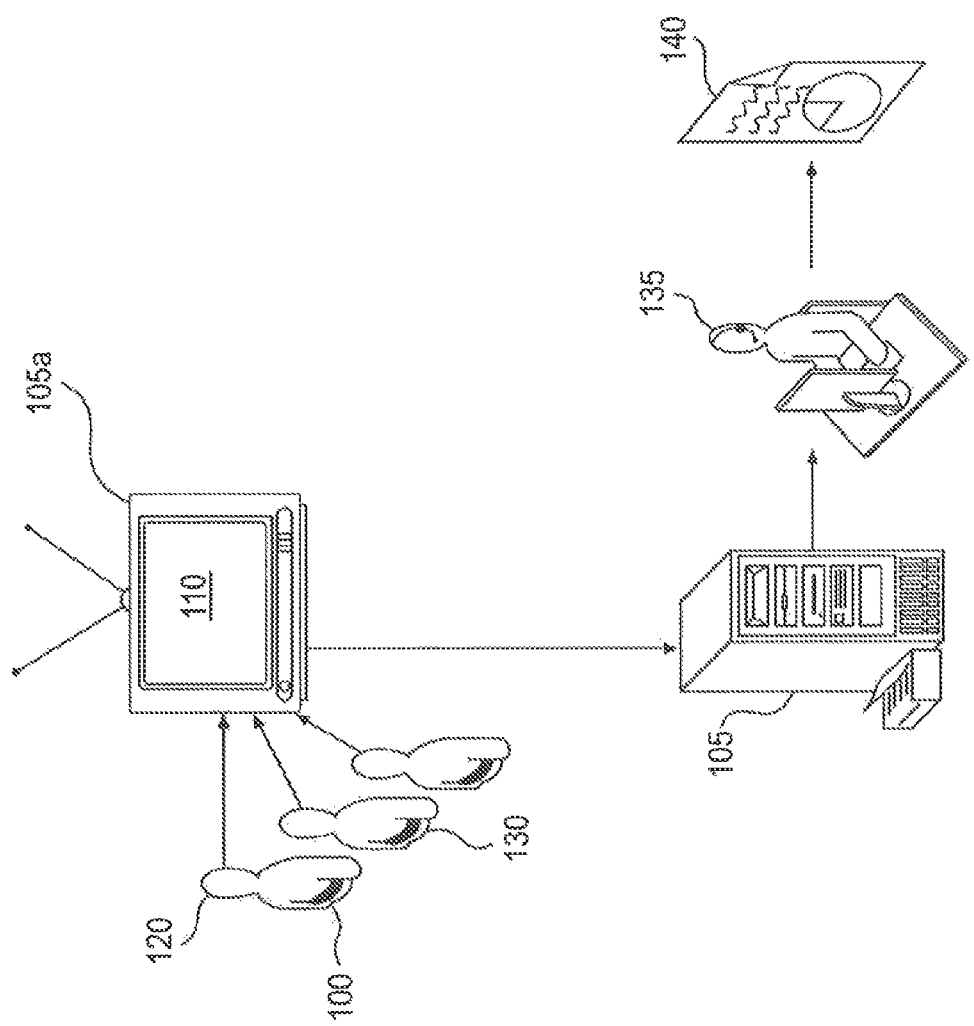

METHOD AND SYSTEM FOR GATHERING AND COMPUTING AN AUDIENCE'S NEUROLOGICALLY-BASED REACTIONS IN A DISTRIBUTED FRAMEWORK INVOLVING REMOTE STORAGE AND COMPUTING

CROSS REFERENCE TO RELATED APPLICATIONS

This application is a continuation-in-part of U.S. patent application Ser. No. 13/405,611, filed Feb. 27, 2012, now pending. This application also claims priority to U.S. Provisional Patent Application No. 61/603,521, filed Feb. 27, 2012. Each of these applications is incorporated herein by reference in their entirety.

FIELD OF THE INVENTION

The present invention relates to systems and methods for measuring biologically and behaviorally based responses to content in targeted demographics and locations. More specifically, the present invention relates to systems and methods for implementing remote monitoring of unconscious biologically based and behaviorally based responses when presented with target stimuli.

BACKGROUND OF THE INVENTION

There are many different kinds of audio, visual and audio-visual presentations and activities that people are exposed to every day. These presentations serve as sensory experiences that stimulate our senses and are known to result in biologically based responses that can be measured electronically and mechanically (for example, heart rate, respiration rate, blood pressure, and skin conductance).

A commonly used approach in making measurements for evaluating these presentations is that of interrogation, wherein the television/media viewer and/or Internet user and/or game player is asked to identify himself or herself as a member of the television/media audience or as an Internet user or as a game player. In connection with television viewing, this inquiry is usually done by means of an electronic prompting and data input device (for example, as in a Portable People Meter by Arbitron, Inc.) associated with a monitored receiver in a statistically selected population and monitoring site. The member identification may also include age, sex, and other demographic data. However, these non-biologically based self-report methods of measuring audience response are known to be highly error prone.

In fact, personal logs are subjective resulting in recall biases, home monitoring devices require event-recording by the person and suffer low compliance, while digital monitoring of cable and internet signals cannot identify which household member or members are in the audience nor can they evaluate the level of responsiveness by those members. Other methods of self-report offer valuable data, but are highly error prone and cannot track the moment-to moment responses to media consumption and participation in interactive activities.

In particular, with the development of the Internet and its expansion into many everyday activities, people are constantly exposed to interactive media and activities. Nonetheless, the ability to measure and evaluate the user experience, effectiveness, and the usability of these interactive media has been limited. In fact, current methodologies for measuring or evaluating user experience, effectiveness, and usability of websites and other interactive Internet and software media has thus far been limited to traditional self-report and eye-tracking on an individual user basis. These prior art techniques involved asking the individual user questions about the experience and evaluating where the user was looking during the interactive activity.

These prior art systems require advanced knowledge of demographic data prior to the implementation of the system. For example, in order to ensure an audience made of selected demographics and geographic regions, the audience must be prescreened to identify individuals and households within the specific geographic regions and within the specified demographic categories. Thus, the only alternative is to select individuals and households at random. However, selecting individuals and households at random does not guarantee that certain demographics and/or geographic areas are available for research.

The majority of systems acquiring biologically based signals for measuring the performance of content stimuli are laboratory-based where participants are brought in to a testing facility and their biologically-based signals are acquired using specialized equipment while watching target content. While attempts have been made to gather EEG data in home environments, compliance by the targeted audience is difficult because there is no guarantee as to whether or not the signals collected remotely are from the targeted person or another member of the household.

Accordingly, the challenges of the current methods and systems include, but are not limited to: (1) security (due to the content being provided over the interact or through a home monitoring device which then creates the possibility of an audience member recording and subsequently distributing the content); (2) carefully selected distribution mandatory (in order to reach a wide array of people and fulfill targeted demographics); (3) errors (due to the heavy reliance on self-reporting); and verification of compliance with study parameters (such as whether the data collected is from the targeted demographic); (5) associated costs with (a) lab-based methods (bringing the audience into the lab are very high) and (b) home-based audience monitoring (the costs of ensuring compliance are high), and for both (a) and (b) ensuring a geographic distribution is not easy and could compound the associated costs); and (6) determination of invalid signals is unavailable until post-processing (which requires additional steps and increases costs).

Thus, a need in the art exists for a system and method that is capable of integrating self report and physiological data and capable of secure distribution. In addition, a need exists for an efficient and cost-effective system and method that is capable of integrating self-report and physiological data that can ensure a wide geographic distribution to an audience. Finally, a need exists for a system that is capable of providing results from a wide variety of demographic categories when monitoring unconscious biologically based and behaviorally based responses to track performance of target stimuli.

Using a cloud infrastructure to implement such a system and method allows for lower maintenance costs, high availability, security, and reliability, faster distribution/propagation of content to a wide-range of geographic locations, scalability based on workloads (number of projects), and adjustability for specific geographic locations.

SUMMARY OF THE INVENTION

The present invention is directed to a method of determining a measure of response of remotely located audiences to a target stimulus at a plurality of locations including the steps of: providing at each location at least one biologically based sensor operable to measure at least one unconscious biological response for each member of an audience; providing at each location a computer system operable to receive data representative of the at least one unconscious biological response, wherein the computer further includes a memory for storing the data; receiving at each location at least one target stimulus; exposing each member of the audience at each location to a presentation of the at least one target stimulus; obtaining a first set of data representative of the at least one unconscious biological response from the presentation for each audience member; and transmitting the first set of data to a central location for analysis.

In one embodiment, the method further includes the step of analyzing the first set of data and reporting the results. In another embodiment, the method further comprises the step of comparing the first set of data to data from a standard testing template of content stimuli.

The at least one unconscious biological response may include heart rate, galvanic skin response, respiration, and motion. In one embodiment, the at least one biologically based sensor includes a first sensor operable to measure heart rate and a second sensor operable to measure galvanic skin response.

In another embodiment, the method further includes the steps of providing at each location at least one of a biologically based measuring device operable to measure EEG, at least one neuroimaging modality, or a combination thereof, a device operable to measure facial expression, a device operable to measure eye movement, or combination thereof, wherein the computer system is operable to receive and store data representative of EEG, at least one neuroimaging modality, facial expression, eye movement, and combinations thereof; obtaining a second set of data representative of at least one of EEG, at least one neuroimaging modality, facial expression, eye movement, or combinations thereof from the presentation for each audience member; and transmitting the second set of data to a central location for analysis.

The method may also include the step of receiving demographic information in at least one demographic category from each member of the audience. In one embodiment, the at least one demographic category comprises age, gender, race, income, and educational background. In another embodiment, the system may aggregate the demographic information for each demographic category, receive a terminal value for each demographic category, receive an alternate target stimulus, and expose an individual audience member within a certain demographic category to a presentation of the alternate target stimulus if the terminal value for the certain demographic category has been reached.

The present invention is also directed to a system for determining a measure of response of a remotely located audience to a target stimulus including: at least one biologically based sensor operable to measure at least one unconscious biological response for each member of an audience; a computer system operable to receive data representative of the at least one unconscious biological response, wherein the computer system further includes a memory capable of storing the data, wherein the system is capable of receiving at least one target stimulus, wherein the system is capable of exposing each audience member to a presentation of the target stimulus, wherein the system is capable of receiving data representative of the at least one unconscious biological response for each audience member from a plurality of locations and audiences, and wherein the system is capable of obtaining demographic information from each member of each audience in each location.

In one embodiment, the system is self-contained in a single unit. The single unit may be a kiosk, a smart phone, or a tablet. In another embodiment, the demographic information includes a plurality of categories comprising at least one of age, gender, race, income, and educational background.

The at least one unconscious biological response comprises heart rate, galvanic skin response, respiration, and motion. The system may also further include at least one biologically based measuring device operable to track eye movement, wherein the system is capable of receiving data representative of the eye movement for each audience member from a plurality of locations and audiences. In another embodiment, the system may further include at least one device operable to measure facial expressions at predetermined time intervals, wherein the system is capable of receiving data representative of the facial expressions for each audience member from a plurality of locations and audiences. In yet another embodiment, the system may also further include at least one device operable to measure EEG, at least one neuroimaging modality, or combinations thereof, wherein the system is capable of receiving data representative of the EEG, at least one neuroimaging modality, or combinations thereof for each audience member from a plurality of locations and audiences.

In still another embodiment, the system may include a plurality of biologically based sensors to measure unconscious biological responses such as heart rate, galvanic skin response, respiration, and motion, at least one biologically based measuring device operable to track eye movement, at least one device operable to measure facial expressions at predetermined time intervals, and at least one device operable to measure EEG, at least one neuroimaging modality, or combinations thereof, any of all of which may be operable depending on the particular target stimuli presented. For example, the system may include all of the sensors above, but a client may request only particular measurements for any given presentation.

The system may also be capable of receiving a capacity value for each demographic category and location for a presentation of the target stimulus, wherein the system is capable of receiving an alternate target stimulus, and wherein the system is capable of exposing an audience member to a presentation of the alternate target stimulus when the capacity value is obtained. In one embodiment, the capacity values are distributed equally for each location. In another embodiment, the system is capable of receiving target demographic density information for each location. In still another embodiment, the capacity values are allocated proportionate to the target demographic density information in the location.

The system may also be capable of reporting the data representative of the at least one unconscious biological response for each audience member from a plurality of locations and audiences and demographic data to a central location. In another aspect, the system may be operable to provide a plurality of target stimuli based on at least one of geographic location or demographic category.

The present invention also relates to a system and method of implementing a scalable, reliable, efficient and cost effective distributed biometric monitoring and data acquisition system. In one embodiment, the system and method involves cloud-based server-client technology to allow for monitoring of a plurality of members of an audience or group in asynchronous geographically distributed environments and collecting the participants' physiological, eye tracking, and facial expression reactions to the presented content.

The present invention is also directed to a system for determining a measure of response of a remotely located audience to a target stimulus including: at least one biologically based sensor located in a remote station operable to measure at least one unconscious neurologically based brain response for each member of an audience; a computer system operable to receive a first set of data representative of the at least one unconscious neurologically based brain response for each audience member from a plurality of locations and audiences, wherein the computer system further includes a remote memory capable of receiving and storing the first set of data, wherein the system is capable of receiving and storing a plurality of target stimuli, wherein the system is capable of exposing each audience member to a presentation of the target stimulus, and wherein the system is capable of obtaining demographic information from each member of each audience in each location.

In one embodiment, the at least one unconscious neurologically based brain response includes skin conductance, heart rate, respiration, EEG, head movement, or a combination thereof. In another embodiment, the computer system is operable to receive a second set of data representative of at least one other unconscious neurologically based brain response for each audience member, and wherein the at least one other unconscious neurologically based brain response includes facial expression, eye tracking, or a combination thereof.

In still another embodiment, the system includes a remote location software module including a recording module to obtain the at least one other unconscious neurologically based brain response. The recording module may include a camera, a video recorder, an eye tracker, or a combination thereof.

In one embodiment, the at least one target stimulus is stored remotely from the remote station. In another embodiment, the system is capable of selecting the presentation of the target stimulus from a plurality of target stimuli based on a plurality of factors, wherein the plurality of factors includes the demographic information. The demographic information may include at least one of age, gender, race, income, educational background, or a combination thereof.

The present invention is also directed to a system for determining a measure of response of a remotely located audience to a presentation including: at least one biologically based sensor located in a remote station operable to measure a plurality of unconscious neurologically based brain responses for each member of an audience; a computer system operable to receive a first set of data representative of the plurality of unconscious neurologically based brain responses for each audience member from a plurality of locations and audiences, wherein the computer system further includes a remote memory capable of receiving and storing the first set of data, wherein the system is capable of receiving and storing a plurality of target stimuli, wherein the system is capable of exposing each audience member to a presentation, and wherein the system is capable of obtaining demographic information from each member of each audience in each location.

In one embodiment, the at least one biologically based sensor includes a first sensor operable to measure heart rate and a second sensor operable to measure galvanic skin response. In another embodiment, the system further includes a recording module located in the remote station operable to measure at least one of facial expression, eye movements, or combination thereof. In still another embodiment, the system is operable to receive a second set of data representative of the recorded facial expression, eye movements, or combination thereof. The remote memory may be capable of receiving and storing the second set of data.

In another embodiment, the system is capable of receiving a capacity value for each demographic category and location for a presentation, wherein the system is capable of receiving an alternate presentation, and wherein the system is capable of exposing an audience member to a presentation of the alternate presentation when the capacity value is obtained. The capacity values may be distributed equally for each location. In yet another embodiment, the system is capable of reporting the first set of data for each audience member from a plurality of locations and audiences and demographic data to a central location.

BRIEF DESCRIPTION OF THE DRAWINGS

Further features and advantages of the invention can be ascertained from the following detailed description that is provided in connection with the drawings described below:

FIG. 3 is an example of an embodiment of the method of the invention.

DETAILED DESCRIPTION OF THE INVENTION

Figure 1:
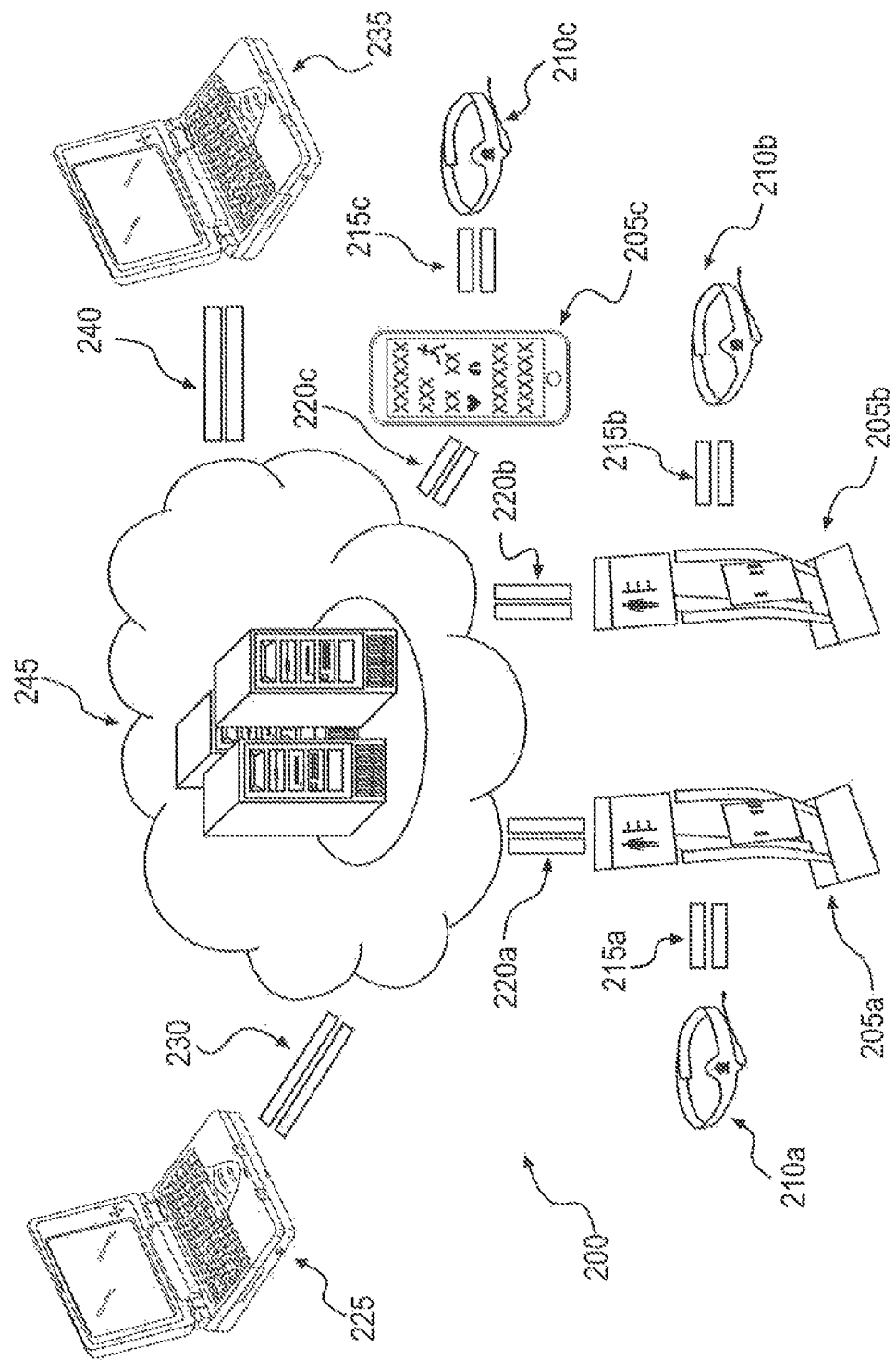
FIG. 1 is a schematic of the physical hardware incorporated into the system according to one embodiment of the invention.

The present invention is directed to a system and method of measuring biologically and behaviorally based responses to content in targeted demographics and locations using cloud infrastructure. In one embodiment, the system and method involves cloud-based server-client technology to allow for monitoring of a plurality of members of an audience or group in asynchronous geographically distributed environments by using remotely located stations units and storing and processing the content, parameters, data (physiological reactions, eye tracking data, facial expression data, self-report data), and results of the project in the cloud.

The present invention is directed to a research method and system for measuring an audience's physical, behavioral, biological and self-report responses to a sensory stimulus and reporting the results to a central location. In particular, the invention is directed to a method and system for exposing an audience to a stimulus, measuring one or more unconscious responses of one or more persons being exposed to a sensory stimulus, presentation, or interactive activity, and reporting the results to a central location. The invention allows for screening of relevant participants using client-specified demographic-targeting criteria, in geographically dispersed environments, identifying and detecting whether or not the participants have valid signal ranges during a test, thereby eliminating over-recruits and costs. Furthermore, the invention can be used to determine whether the presentation or interactive activity is more effective in a population relative to other presentations and other populations (such as may be defined by demographic, geographic, or psychographic criterion).

The sensory stimulus, presentation, or interactive activity may include an audio, visual or audiovisual stimulus, such as a sound or sequence of sounds, a picture or a sequence of pictures including video, or a combination of one or more sounds and one or more pictures, including video. The stimulus can be prerecorded and played back on a presentation device or system (e.g., on a television, video display, projected on a screen, such as a movie) or experienced as a live performance. The stimulus can be passive, where the audience experiences the stimulus from a stationary location (e.g., in front of a television or video screen) or the stimulus can be interactive where the audience is participating in some form with stimulus (e.g., simulated roller coaster ride, shopping experience, computer game, virtual reality experience or an interactive session via the internet).

The deployment of the specific projects is described in greater detail below. Briefly, through the use of remotely located units (e.g., kiosks or smart phones or tablets), the project may include the steps of: providing at each location at least one biologically based sensor operable to measure unconscious biologically based responses and/or behaviorally based responses for each member of an audience; providing at each location a computer system operable to receive data representative of the unconscious biologically based response and/or behaviorally based response; receiving from the cloud infrastructure at each location at least one target stimulus; exposing each member of the audience at each location to a presentation of the at least one target stimulus; obtaining data representative of the at least one biologically based response and/or behaviorally based response from the presentation for each participant.

According to one aspect of the invention, the system includes a display device, a processor, and at least one biologically based sensor operable to measure unconscious biologically based responses. Preferably, the system is operatively connected to a server allowing for data to be sent and received by the system. In one embodiment, the system is equipped to simultaneously expose content (e.g., a sensory stimulus, presentation, or interactive activity) to a plurality of audience members. The system may also be operatively connected to one or more sensors for measuring eye movement/pupil dilation. According to one aspect of the invention, the system also includes one or more self-report surveys.

In one embodiment of the invention, a system that captures specific, unconscious biologically based signals (such as skin conductance and heart rate), optionally with other unconscious biologically based signals (such as respiration and movement), may be built using sensors that maintain the portability of the system and thus allow the system to be deployable in various geographic locations using cost-effective equipment. Additional unconscious responses or signals may also be captured by the system at varying incremental costs. For example, eye tracking, facial coding, EEG, fMRI, PET scan, MEG and the like may be used to capture additional data in response to content.

In one embodiment, the entire system may be contained in a single unit, which beneficially allows the system to be easily and rapidly deployed to a variety of locations. For example, the system may be implemented in a kiosk and deployed to a variety of public locations including, but not limited to, shopping malls, movie theatre lobbies, hotel lobbies, airport terminals, train stations, food courts, car dealership showrooms, or other public venues. The system may also be implemented in a smart phone, tablet, or the like. The ability to distribute the system to a wide variety of locations allows for a large sample population. In addition, the ability to deploy the system to specific locations allows for the ability to reach a target audience without subjecting the audience to the burden of travelling to a lab. For example, an advertiser interested in feedback from football fans could deploy a kiosk to a football stadium instead of identifying football fans in the general population and attempting to lure the fans into a lab for testing.

In one embodiment of the invention, the system is capable of displaying content relevant to the location or independent of the location. For example, in car showrooms the content displayed and tested may be related to only new cars, and unrelated to the location of the showroom. In the alternative, content related to a specific location or relevant to the population in the specific location may be displayed and tested.

According to one aspect of the invention, the system is capable of receiving instructions and content. Thus, the system may receive specific content directly from a company/client seeking feedback on an advertisement, television show, movie, website, etc. without requiring submission of the content to the system provider and or involving delay while the system provider uploads the content for review by an audience. In addition, the system is capable of transmitting the measurements and data. Preferably, the system transmits or sends data at a predefined interval. For example, the data collected by the system may be sent on a daily basis, weekly basis, or other suitable time frame. The system may also detect "idle-times" between sessions of two participants and transfer the data to the central location. According to one embodiment, the system is programmable to alter the data collection and transmission period as desired or automatically optimize to ensure less interruption of the content-viewing on the kiosks, smart phones, tablets, or the like.

Display Device

In one embodiment of the invention, any suitable display device known in the art may be employed. Suitable display devices include, but are not limited to, televisions, LCD screens, touch screens, 3-D displays, movie screen, head-mounted displays, plasma screens, a desk-top, hand-held or wearable computer device, gaming console, home or portable music device, or any other device for the presentation of passive or interactive audio, visual or audio-visual presentation. The system could also be displayed on user devices in the location such as mobile phones and other devices that include a display. A skilled artisan would readily appreciate that other technologies may be employed that are capable of exposing an audience member to a sensory stimulus, presentation, or interactive activity.

Sensors

Responses that are based in human biology can have multiple physiologic and behavioral correlations. Thus, embodiments of the present invention may include a plurality of devices and sensors to measure the unconscious biologically based responses.

One aspect of the invention includes collecting at least one measurement by eye-tracking. The eye-tracking measures can include, but are not limited to, visual attention as estimated by gaze location, fixation duration, pupil dilation, and movement within a localized area. The system can use eye-tracking or other technology to isolate specific elements, areas or moments of interest for further analysis or processing. In accordance with one aspect of the invention, the system can track what content is being viewed, who is viewing the content (including by gender and demographic/psychographic profile), which areas or sub-areas of the content are being focused on by each individual and which measured responses of the audience correspond to the viewed content.

Another aspect of the present invention includes collecting unconscious biologically based responses by measuring galvanic skin response (GSR), heart rate, heart rate variability, brain-wave activity, respiration activity, facial emotional responses (collected by video or other similar methods), eye tracking, and combinations thereof. In a preferred embodiment, at least two measures of unconscious biologically based responses are obtained by the system.

The biologically based sensors or monitoring devices for measuring the unconscious biologically based responses may include any of a number of commercially available or other sensors known in the art for measuring such responses. In accordance with one aspect of the invention, the least invasive and obtrusive sensors with the most comfortable form factor should be chosen to minimize disruption of the experience. Preferably, the sensors should allow participants to experience the presentation or test stimulus "as if" they were not being monitored at all. Suitable biologically based sensors include but are not limited to wearable devices such as "smart" garments, wrist bands, shirts, sleeves, arm bands, cameras, watches, and head-gear. Multiple combinations of sensors can be used depending on the sensory stimulus, population, and location of the monitoring. In a preferred embodiment, the biologically based sensor is an arm band.

A third aspect of the present invention includes collecting behavioral data from the participants. Behavioral type responses can include, but are not limited to, facial micro and macro-expressions, head tilt, head lean, body position, body posture, body movement, and amount of pressure applied to a computer mouse or similar input or controlling device. One or more cameras and/or pressure sensors may be used in accordance with this aspect of the invention to collect behavioral data.

Self-report type measures can include, but are not limited to, survey responses to items such as perception of the experience, perception of usability or likeability of experience, demographic data, level of personal relevance to user, attitude toward content or advertising embedded in the content, intent to purchase product, game or service, and changes in responses from before and after or pre-post testing. According to one aspect, the system includes one or more data entry device. The self-report device can be any of the well-known devices for permitting an audience member to report their response to a presentation or interactive activity. Typically, self-report devices include a knob, a slider or a keypad that is operated by the audience member to indicate their level of interest in the presentation. By turning the knob, moving slider or pressing a specific button on the keypad, the audience member can indicate their level of interest in the presentation or interactive activity. Alternatively, self-report device can be a computer keyboard and/or mouse that an audience member can use to interact with the presentation. Mouse movements in association with icons or elements on the computer screen can be used to indicate levels of interest. In addition, the mouse or other input device can include sensors, such as force and pressure sensors for measuring the forces applied to the mouse by the audience members. Alternatively, keyboard keys (up arrow, down arrow, page up and page down), can used to indicate levels of interest. In addition, the user can type in responses to questions or select answers to multiple choice questions. Suitable data entry devices include, but are not limited to, a mouse, keyboards, knobs, buttons, sliders, touch screens, voice recognition technology, and variations thereof. According to one aspect, the audience member enters information manually. In the alternative, one or more administrators may enter the information for an audience member.

Computer Systems and Cloud Infrastructure

Some or all of the sensor data and input data can be transferred either by wire or wirelessly to the computer system and further transferred to a data processing system. Alternatively, some or all of the sensor and input data can be transferred directly to the data processing system by wired or wireless network. The network can utilize most communication technologies, including RS-232, Ethernet, Wi-Fi, Blue Tooth and Zigbee, for example. In addition, more than one communication technology can be used at the same time, for example, the network can included wired components (such as, Ethernet and digital cable) and wireless components (such as, Wi-Fi, WiMAX and Blue Tooth) to connect different sensors and computer system components to the data processing system. Furthermore, the data processing system can be one computer system or a cluster, group, or network of computer systems. For example, several kiosks containing the systems may be operatively connected to one another via a network.

The computer system may also include a locating device, such as a GPS device, capable of recording and reporting the position of the system via wired or wireless connection. According to one aspect of the invention, the locating device is capable of identifying and reporting the position (direction and distance) of the system in relation to other locations, including but not limited to, towns, cities, landmarks, and other reporting systems in a network of systems.

FIG. 1 generally shows an embodiment of the system 200 of the invention using the cloud infrastructure. In one embodiment, the system and method of the invention is capable of project creation and dissemination via the cloud infrastructure. For example, a specific project, e.g., two advertisements to evaluate for response, would be created using the cloud infrastructure 245. In particular, it is contemplated that the content is created with computer system 225, which in this example scenario includes advertisements, would be uploaded to a specific area in the cloud storage via link 230. In addition, any other content that is intended to be used for the project, e.g., baseline content, specific content for context, anchoring commercials, and the like, would also be uploaded or transferred to the specific area via link 230 in the cloud storage 245. In fact, any one test may include a presentation of a mixed sequence of content stimuli, as well as self-report surveys (before and after the presentation of content stimuli). As such the self-report surveys and the following types of content stimuli may be stored in the cloud 245 for use in the project in the form of content-reels. Each content-reel may have one or more occurrences of the following items in pre-determined orders (to balance for priming and other influences):

1. Baseline content including a variety of standard images such as the International Affective Picture System (IAPS), standard video content to evoke a range of emotions for the audience, and optional standard web content to evoke a range of web experiences;
2. Specific content for context including television programs (e.g., Everybody Loves Raymond), movie trailers, and the like that are typically aired during primetime programming;
3. Anchoring commercials, which include standard commercials (non-target) that are inserted into multiple studies to remove priming effects and to "normalize" across different audience segments and standardize scores; and/or
4. Target content, which includes specific commercials, programs, movies, websites, and the like to be tested/studied for performance/success.
5. Online web content, that is relevant for a client test 6. Online self-report surveys, which may be designed to determine how much the participant likes the prior content that they saw earlier (or about to see later) in the test Once the test is designed, the parameters (and the content-reels) are also stored in the cloud 245 so that the project can be deployed to various geographically-dispersed computers, i.e., individual stations, handheld devices, and the like, generally represented here by 205*a-c*, in fact, in another embodiment, the system and method of the invention also involves using the cloud infrastructure for the creation of demographic allocation tables for distributing quota tables (workload) to various geographic locations.

As such, the content and parameters for the project are transferred from the cloud to the remotely located stations 205*a-c* via links 220*a-c*. The sensors 210*a-c* are connected to the stations 205*a-c* via wired or wireless links 215*a-c*. While three stations are shown in FIG. 1, the present invention contemplates a system that incorporates more or less stations. In one embodiment, a plurality of stations 205 are used in accordance with the invention. For example, the plurality may include at least two stations 205. In another embodiment, the plurality may include at least five stations. In yet another embodiment, the plurality may include at least ten stations. In contrast, the system may include a single station 205. In another embodiment, the system may consist of at least one portable station 205. For example, a suitable portable station may include a laptop computer, a monitor, a mobile device, or any combination thereof.

Likewise, the data collected from the remote locations 205 are received and stored in the cloud 245 for processing (e.g., analyzing and reporting). In this regard, the biologically based and/or behaviorally based responses to the presentation by each participant at the geographically dispersed public computers are uploaded to the cloud storage and then transferred to a computer system 235 via link 240 for analyzing and reporting.

It is also contemplated that the cloud infrastructure is similarly capable of analyzing the data using any or all of the methods for predicting audience viewing behavior and measuring user experience for interactive activities described in U.S. Pat. No. 8,296,172 and co-pending U.S. patent application Ser. No. 12/749,376, filed Mar. 29, 2010, Ser. No. 12/426,259, filed Apr. 19, 2009 and Ser. No. 13/089,752, filed Apr. 19, 2011, the entire disclosures of which are incorporated herein by reference, are contemplated for use in analyzing the data collected with the system and method of the present invention. The present invention also contemplates using the cloud infrastructure to aggregate across data acquired from various locations (and for various participants) and creating meaningful analytics insights/reports for specific content.

In another embodiment, the cloud infrastructure includes a neurological database that aggregates reports from various projects into database silos based on category, industry, client, brand, neurological measure, and the like.

Different types of software modules are contemplated for the sensus station versus the cloud. In general, the software modules contemplated by the system of the present invention may include, but are not limited to, at least one neurologically based signal recording module, a signal checking module for quality control, a communicator module, a screening module, a survey module, a content player module, an experience manager, and a syncing/transferring module.

For example, the neurologically based signal recording module may be a module for "controlled" starting and stopping of facial-Video recording (using a webcam at the remote location) during reel play of the target content. In addition, the neurologically based signal recording module may include an sdk module to start and stop eye tracking from an eye tracker.

In sum, as generally illustrated in FIG. 1, a participant using a remote station puts on the biometric sensor device. The software at the remote location/station performs quality control checks and guides the participant/administrator through a series of steps to correct any issues with the sensor device. Once the biometric signals are deemed valid, the participant is guided to a screener section to specify the demographics of the participant to determine a stimulus/presentation to be shown to the participant.

The station then shows and simultaneously times the various pieces of content-stimuli associated with the particular presentation in addition to recording the biometric signals during the presentation. At the end of the session, the system walks the participant through any optional surveys that need to be completed. An additional quality control step to check whether the signals were valid for the participant during the presentation is then employed. The folder for the session/presentation may be automatically uploaded (at the end of presentation) or scheduled for upload to the cloud at a predetermined time. In one embodiment, the folder may include content (reel runs) timings, biometrics, demographics, participant's video (for computing facial expressions), eye tracking info, and any other associated data. Once the folder and included data is in the cloud 405, it may be aggregated across different participant sessions and to analyzed using specific software for the biometrics and self-report, as well as software for eye tracking and facial coding, and Visualization software.

Figure 2:
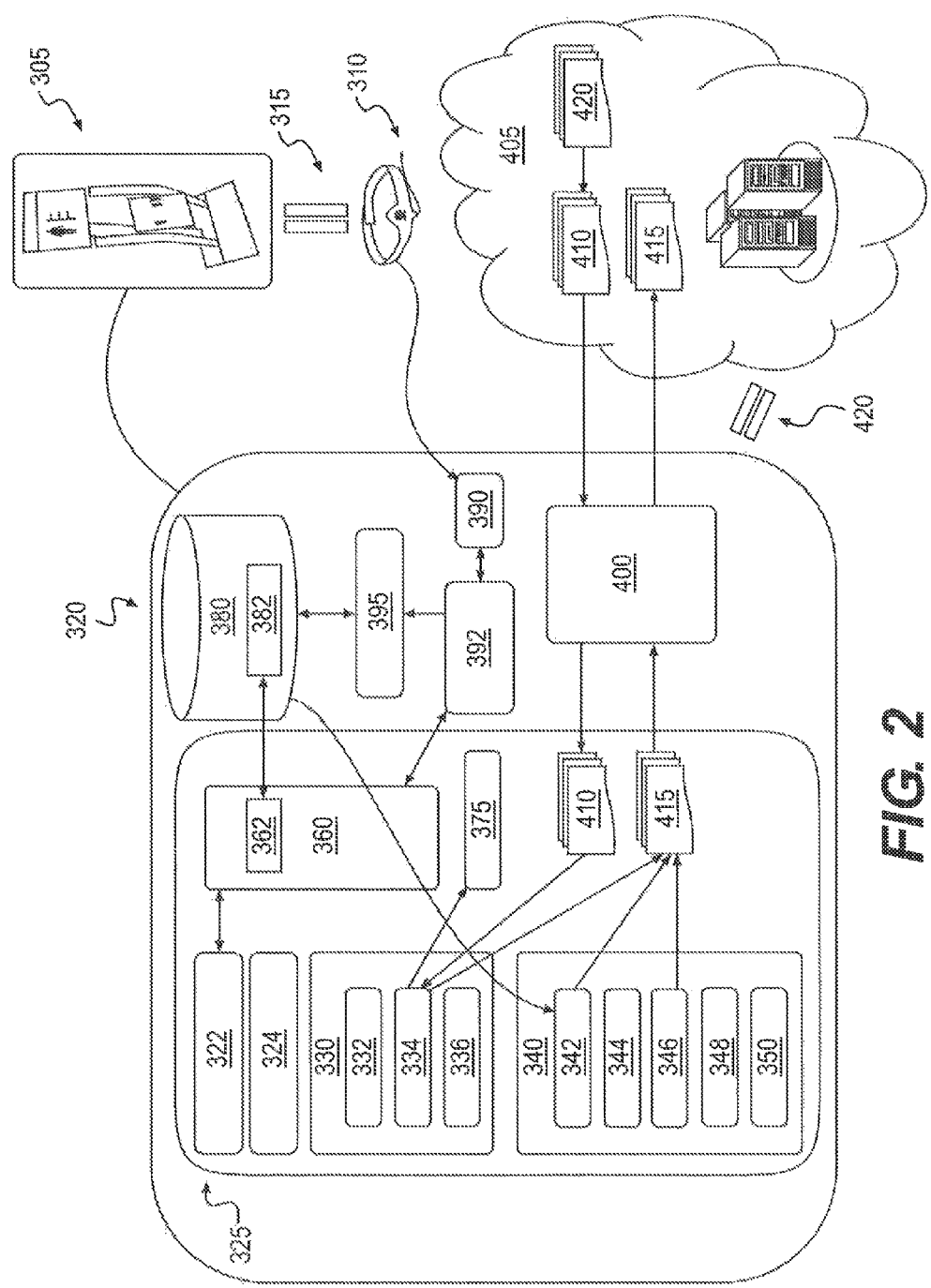
FIG. 2 is a schematic of the software components according to one embodiment of the invention.

While those of ordinary skill in the art would recognize that other modules/steps not specifically mentioned may be incorporated into the workflow modules, FIG. 2 provides one embodiment of the overall workflow/modules of the system of the present invention with remote administration of a presentation/stimulus to participants with biometric monitoring.

In particular, as shown in FIG. 2, the remote location (shown here as 305) may include a software module 320 for the remote location, unit, or station 305. In this regard, the module 320 may include a Sensus software application 325 that, itself, may include various subset modules. In addition, the module 320 may include functionality to receive and process the data from the sensor 310. In one embodiment, receiver module 390 may be Bluetooth or other wireless networking software or the like that transmits the data collected with the sensor 310 to the software module 320 as streaming raw data. The raw data in 390 may be dumped into a first processing module 392 that processes/converts the data (e.g., from r-r intervals to HR) and sends to second processing module 395 for further action. In particular, the second processing module 395 aggregates the data into smaller sampling units. The database 380 stores the specific data 382 after aggregation.

A communicator module 360 checks the data in the database 380 at predetermined periodic intervals to determine whether the signals being collected are within acceptable ranges, creating a feedback 362 that is provided to the user interface 320. The user interface 322 includes a display that demonstrates proper functioning of the sensor 310, remote station 305, and other elements of the system. For example, if the heart rate signal being collected is flat, the user will receive instructions via user interface 320 to modify the attachment means for the sensor 310 by repositioning, tightening, or changing the attachment means or replace the sensor 310. As discussed in greater detail herein, the attachment means may vary based on the sensor. Any suitable apparatus that allows the sensor to contact the user is contemplated. For example, if the sensor is to be wrapped about the arm of the user, the attachment means may be a strap, a sleeve, or the like. This quality control loop between 310, 380, 360, and 322 will continue until the system is functioning as expected (i.e., the signals are within acceptable parameters). If after multiple attempts to adjust the attachment means and/or sensor do not result in the signals being within acceptable parameters, the audience member/user is released and the data collection is reinitiated with another audience member/user. This module simplifies the quality control check over other conventional neurological devices. Accordingly, administrative personnel with little to no training may operate the system of the invention.

After a successful quality control check, the user demographic information (discussed in greater detail below), is collected at 325. The demographic information is relayed to a central (remote) server that manages the capacity for each content-reel and demographic segment, determines the specific content reel to be played, and obtains the specific content reel from the server. In one embodiment, the specific content reel includes a baseline segment, a context segment (e.g., a program or movie trailer), buffer advertisements, anchor advertisements, target content 334, and various combinations thereof. In this context, the target content 334 may include target advertisements. In another embodiment where the target content 334 are target program trailers, movie trailers, or the like, the specific content reel 334 includes a baseline segment, target content 334, buffer advertisements, anchor advertisements, and various combinations thereof. The content player module 330 will then play the specified content reel including the target content 334 for the demographics collected at 325.

The project definition 410, which will use a predefined set of rules/tables (discussed in greater detail below) relating to the collected demographic information in 325 as shown in 420, to determine suitable target content to be played by the content player 330 (334), as well as the set content reels for the project. The project definition is a replica of the project definition 410 in cloud 405, which also contains a demo quota manager 420. The project definition 410 is pushed to the remote station 305 and operated by the software module 320 via 400. In addition, the content player module includes pre- and post-surveys 332 and 336 that require user input. The target content 334 and the content player reel run log containing timing information is sent to the replica session data folders 415 in the software module 320 and later synched to the session data folders 415 in cloud 405 via 400.

A recording module 375 may include eye tracking capability, video recording capability, static image recording capability, EEG recording capability, and combinations thereof. For example, the recording module 375 may receive a first signal from the content player 330 that the target content 334 will begin. The first signal will trigger the start of the recording. Likewise, once the target content 334 stops, a second signal received by the recording module 375 will stop the recording module from acquiring further data. The recording module is operatively connected with the session data folders 415 so that the data collected from 375 may be synched/transferred from the session data folders 415 to the cloud 405 via 400.

The administrator module 340 may include an archive/data transfer to transfer the data from 360/362 into the session data folders 415 for eventual synching/transferring to the cloud 405 via 400. A closing session message will appear in 344. The actual transfer/synching of data in the session data folders 415 to the cloud 405 is performed in 346. The server update 348 may include notes from the administrator about the overall session, an automatic update from the Sensus software application 325 after performing a session level quality control check to indicate whether the biometric data collected during the reel play in 330 was acceptable. Based on this update, the demographic quota tables (discussed in greater detail below) will be updated (as one less participant to recruit for that demographic). The sensor status 350 may include administrator notes about the sensor (including any problems with the sensor or the sensor attachment means) during the session. The module 346, which synchronizes the data with the cloud 405, may happen at the completion of an audience member/user session (providing the data collected is not too large for transfer) or during a period of inactivity. Once transferred, the session data folders in software module 320 are marked as transferred and queued for deletion at a later, predetermined time.

The software module for the cloud 405 may include software for project creation (to create reels or presentations) which would be stored in project definition folders 410 for synching/transferring to the software module 320 when needed. In addition, the software module for the cloud 405 may include software for project deployment, tracking (e.g., a dashboard), analytics and visualization, and other software to perform the methods described in U.S. Pat. No. 8,296,172 and co-pending U.S. patent application Ser. No. 12/749,376, filed Mar. 29, 2010, Ser. No. 12/426,259, filed Apr. 19, 2009, and Ser. No. 13/089,752, filed Apr. 19, 2011. For example, tracker software may allow project coordinators to track general details of a specific project, e.g., general deployment, demographic quotas, and the like, as well as specific details for a station, e.g., active or in-progress sessions, reports. In addition, the tracking software may allow a particular station or terminal to be added, deleted, or modified.

The Presentation (or Stimuli)

The presentation may consist of a mixed sequence of content stimuli, self-report surveys (before and after the presentation of content stimuli). The presentation may include, but is not limited to, the following types of content stimuli:

1. Baseline content including a variety of standard images (modeled after the International Affective Picture System (IAPS)), standard video content to evoke a range of emotions for the audience, and optional standard web content to evoke a range of web experiences;
2. Specific content for context including television programs such as Everybody Loves Raymond that are typically aired during prime-time programming;
3. Anchoring commercials, which include standard commercials (non-target) that are inserted into multiple studies to "normalize" across different audience segments and standardize scores; and/or
4. Target content, which includes specific commercials, programs, movies, websites, and the like to be tested/studied for performance/success.

For example, in one embodiment, the target content is a television show. In another embodiment, the target content is a website or page of a website. In addition to content stimuli, the demographics of audience members may be determined through a screener or other suitable method. In this aspect, a 'pre'-survey to assess the inclination toward client branding before the target content is presented and/or a post-survey to assess the same post-presentation is also contemplated.

Geographic Consideration

In one embodiment, the system is capable of identifying its geographic location including, but not limited to, city, zip code, state, county, longitude and latitude and any specific ID that is unique to a location. This advantageously allows the client to expose various content stimuli to audiences in different geographic areas. The system may also be capable of aggregating the number of responses for a particular geographic region, or for a combination of geographic region and targeted demographics. The geographic area may be predefined, or programmable. For example, a predefined region of the south east United States may include all data from Florida, Georgia, South Carolina, North Carolina, Alabama, Tennessee, Mississippi, and Virginia. In the alternative, a client may define a region, such as a specific radius surrounding a city. The system is capable of determining whether it is located within the specified boundaries. Which further refines the geographic analysis of the data collected. In one embodiment, the system aggregates the number individual audience members exposed to the stimulus in a geographic area. According to one aspect, a predefined number of audience members may be set for a particular content stimulus in a particular geographic area. In one aspect, the system may not consider audience members that have invalid signals during the presentation (in the predefined number/quota to be reached). For example, if an audience member has a "flat" skin conductance response for specific durations of the stimuli, it would be considered invalid. Similarly, if the heart rate data is above and/or below a set threshold, e.g., below 30 beats per minute (bpm) and above 190 bpm, the signal would be considered invalid. Once the predefined number has been reached, the system displays an alternate content stimulus. According to one aspect of the invention, the system is capable exposing specific content for a specific geographic region. For example, a regional advertiser may specify that an advertisement only be shown in kiosks within a specific region of the country. In addition, the system is capable of generating and sending a notification when a predetermined number of participants for a particular geographic area is reached.

Demographic Consideration

In one embodiment, the system is capable of identifying and aggregating demographic information. For example, the system may prompt a user to identify at least one of age, gender, race, employment status, education level, or other demographic category. According to one aspect, the system is capable of receiving a predefined limit or threshold value for each demographic category and aggregating responses for each demographic category. The system displays an alternate stimulus to audience members of a specific category once the predefined limit for the category has been reached. In one embodiment, the system is capable of combining one or more demographic categories. For example, the system is capable of receiving targeted demographics, such as women aged 18-34, and displaying a particular content stimulus to audience members within the targeted demographic. When a predefined number of responses for a targeted demographic have been reached, alternate stimulus content will be displayed to subsequent members of the targeted demographic. In addition, the system is capable of generating and sending a notification that a predetermined number for a particular demographic category area has been reached.

According to one embodiment, the system is capable of receiving demographic information for a particular location. For example, based on information obtained through the census or another source, the system may be able to receive information including any of the demographics discussed above. The system can allocate a threshold value for each targeted demographic category in proportion to the density of the demographic category in a specific location. In the alternative, the system can allocate the threshold number for a demographic category equally in each location. In addition, the system can receive the threshold value at any time before, during, or after interaction with an audience member.

In one aspect of the invention, the system can show different content for different targeted demographic population. Since the demographics can be distributed across various geographical regions, the system can divide the pre-defined quota of demographics across the regions. For example, as shown below in Table 1, a client may specify a specific quota for a targeted demographic. The system would then distribute this "quota-to-fill" across different geographic locations such as in Table 2.

TABLE 1

Audience Member Quota to Fill

| | Male | Female | Young | Old | Core | Non-Core | Reel | Subject-Ranges |
|---|---|---|---|---|---|---|---|---|
| Male | 30 | X | 15 | 15 | ANY | ANY | 1 | 1-45 |
| Fem | X | 30 | 15 | 15 | ANY | ANY | 2 | 30-60 |

TABLE 2

Audience Member Quota Allocated to Each Location

| Location | Gender | Male | Female | Young | Old | Core | Non-Core | Reel | Subject-Ranges |
|---|---|---|---|---|---|---|---|---|---|
| Boston | Male | 30 | X | 15 | 15 | ANY | ANY | 1 | 1-22 |
| Boston | Fem | X | 30 | 15 | 15 | ANY | ANY | 2 | 30-45 |
| LA | Male | 30 | X | 15 | 15 | ANY | ANY | 1 | 23-45 |
| LA | Fem | X | 30 | 15 | 15 | ANY | ANY | 2 | 46-60 |

In one aspect of the invention, the quota may be pre-distributed equally (or based on capacities of the locations) across locations that can cater to the targeted demographics. In another aspect of the invention, the quota may be managed by as central server and allocated on a one-by-one basis per request.

According to one aspect of the invention, the system is capable of reporting all of the measured data (e.g., unconscious biologically based signals including, but not limited to, heart rate, skin conductance, eye-tracking, facial expressions, and EEG) for any combination of demographic category and geographic region.

Additional Features

The system is operable to report the measured unconscious biologically based responses, as well as the geographic and demographic data collected. According to one aspect, the system is operatively connected (e.g., wired or wireless) to a server. The server may be operatively connected to a centrally located processing computer that conducts an analysis of all of the data gathered and generates a report of the results. In addition, each individual system may be operatively connected to other individual systems in different locations. For example, a kiosk located in Miami may be operatively connected to a kiosk in a Fort Lauderdale via the cloud infrastructure shown in FIG. 1.

In one embodiment, the system is operable to aggregate the data collected for each system and for an entire network of systems. In addition, the system is capable of aggregating data for each geographic area and demographic category. According to one aspect of the invention, the aggregation rate is programmable into the system. For example, the system may be set to aggregate data on a daily basis, weekly basis, or monthly basis, or immediately after each audience member test. Thus, an analysis of the data may be made over specified time periods further enhancing the ability to interpret the results.

According to one aspect of the invention, after aggregating data for a specified period, the system is capable of sending a report. The report may include demographic data including the number of audience member participants in any demographic categories that are below a set value. In one embodiment, the system is capable of generating a request for more participants in the deficient category. For example, the system may generate an audio and/or visual advertisement that is displayed to entice members of a deficient category to participate. The advertisement may be of any form including signs, text messages, print, social media, video, audio, and combinations thereof. According to one aspect, the system creates a prompt, instructing an administrator to pursue participants according to a specified need, such as a deficiency in a particular geographic area or demographic category.

In addition, the system may be equipped with the capability to generate incentives and rewards. For example, as a reward or incentive to attract an audience member, the system may be equipped with a printer or similar technology that can automatically generate a coupon, voucher, or gift card. By way of example, a system programmed to display a movie trailer may be capable of supplying vouchers for a free item from the snack bar, or discounted movie tickets. The vouchers are not limited to printed paper, but may also be emailed or electronically transmitted to an audience member. Preferably, the system is programmable to alter (type, amount, or number) the reward or incentive as desired. In one embodiment, the system may offer an audience member a choice from a variety of rewards.

Method

The present invention also directed to a method of obtaining unconscious biological response data, eye-tracking, facial coding, EEG, and other measurements in response to a stimulus. The method may be implemented through the use of the system described above, or in any suitable manner. Preferably, the method is implemented through the use of a self-contained system, such as a kiosk or smart phone, as shown in FIG. 1.

The method includes several steps discussed in greater detail below. However, the order of performing the steps is not limiting, and the method encompasses the steps performed in any logical sequence. In addition, while the method described below does not specifically include a detailed description of the use of the cloud infrastructure, it is contemplated that the cloud infrastructure is incorporated into the method of the invention.

FIG. 3 illustrates an embodiment of the steps of the method. In step 100, at least one biologically based sensor is provided. The sensor is operable to measure at least one unconscious biological response including, but not limited to, galvanic skin response (GSR), heart rate, respiration, and movement. Preferably, at least two unconscious biologically based responses are measured. According to one aspect of the invention, the biologically based sensor comprises one or more wearable devices such as "smart" garments, wrist bands, shirts, sleeves, arm bands, cameras, watches, and head-gear. In a preferred embodiment, the biologically based sensor is unobtrusive and easily removable, such as an arm band. In accordance with one aspect of the invention, step 100 further comprises providing one or more sensors or devices capable of monitoring eye movement and/or pupil dilation. In addition, step 100 may also include providing one or more self-reporting devices including, but not limited to, mouse, keyboards, knobs, buttons, sliders, touch screens, voice recognition technology, and variations thereof. Moreover, step 100 may also include providing one or more video or image recording devices to capture facial expressions and other neurologically based signals that may be incorporated into the analysis with the collected biometric data.

In step 105, a computer system is provided. The computer system may be the system shown as 205 in FIGS. 1 and 305 in FIG. 2. The computer system is operatively connected to at least one biologically based sensor(s) as provided in step 100. In addition, the computer system is operable to receive data from the biologically based sensor(s) and any additional sensors or devices. The computer system also contains a memory for storing data collected by the system. Furthermore, the computer system is capable of sending and receiving data. Preferably, the computer system is operatively connected to a server or cloud. The connection may be wired or wireless and may employ any connection available to a skilled artisan. According to one embodiment, the computer system is operatively connected to a display device 105a. As discussed above, the display device comprises at least one of televisions, LCD screens, touch screens, 3-D displays, movie screen, head-mounted displays, plasma screens, a desktop, hand-held or wearable computer device, gaming console, home or portable music device, or any other device for the presentation of passive or interactive audio, visual or audio-visual presentation.

According to one aspect of the invention, the computer system, biologically based sensors, display device, self-reporting device, and any additional sensors are provided in a self-contained system, such as a kiosk.

The system, which preferably includes the computer system, a display device, and the biologically based sensor(s), receives at least one stimulus in step 110. As discussed above, the stimulus may comprise a sensory stimulus, presentation, or interactive activity that can include an audio, visual or audio-visual stimulus, such as a sound or sequence of sounds, a picture or a sequence of pictures including video, or a combination of one or more sounds and one or more pictures, including video. According to one embodiment, the system receives at least two stimuli. The system may combine the target content/stimuli with other "reference" and "baseline" content/stimuli to make the measurements on the target content/stimuli comparable to prior target stimuli and create scores in analysis. In fact, any of the methods for predicting audience viewing behavior and measuring user experience for interactive activities described in U.S. Pat. No. 8,296,172 and co-pending U.S. patent application Ser. No. 12/426,259, filed Apr. 19, 2009 and Ser. No. 13/089,752, filed Apr. 19, 2011. In one embodiment, the target content/stimuli and any other reference and baseline content may be delivered to the system via the cloud.

According to one aspect of the invention, the system receives the geographic location from a location device, such as a UPS device. In one embodiment, the system receives demographic information about individual members of the audience.

An audience member is exposed to the content stimulus in step 120. The exposure is preferably via an audio and/or visual display device operatively connected to the computer system. In one embodiment, each audience member is exposed to a stimulus individually. In the alternative, a plurality of audience members may be exposed to the stimulus simultaneously.

While the audience member is exposed to the stimulus, the sensors (including biologically based sensors, eye trackers, and self reporting devices) obtain data in step 130, which may be stored on the computer system. The data may be transmitted to the server or cloud for analysis at a central processing facility in step 135. The data, results, and/or analysis may be included in a report in step 140.

In addition to the steps discussed above, several intermediary steps may also be included in the method. For example, according to one aspect, the system receives specific criteria related to each geographic area and demographic category, such as a desired number of participants in each area and category. In addition, the system aggregates the number of audience member participants in each category, area, and combinations thereof. When a preset number of audience member participants within a specific category, area, or combination thereof has been reached, the system offers alternative content to members of that category, area, or combination thereof. For example, the system may receive a limit of 100 participants for the category "18 to 34 year old females within 90 miles of Atlanta" for a particular movie trailer. Upon reaching the limit of 100 participants, the system will no longer display the movie trailer, and may offer a different movie trailer or other content.

Likewise, any steps that fit within the description of the systems shown in FIGS. 1 and 2 with regard to the software driving the remote systems, the analysis of the data, and the transfer to/from and storage of data to the cloud are contemplated as a part of this invention.

In one embodiment, the method includes a step of reporting a deficiency in a specific category, area, or combination thereof. Thus, the method may also include a further step of enticing members of the deficient category, area, of combination thereof by generating an advertisement, incentive, or reward for participation. In addition, the method may also inform an administrator of a deficient category, area, of combination thereof and prompt the administrator to recruit members of the deficient category, area, of combination thereof.

REPRESENTATIVE EXAMPLES

Example 1

The following examples are provided to illustrate an embodiment of the system and method of the present invention. The example is intended to be merely illustrative, and does not limit the scope of the claims to the embodiment presented in the example.

A kiosk is equipped with several components including biologically based sensors, cameras, computer system, touch screen, mouse, LCD display, GPS device, and wireless internet connection. All of the components are connected to the computer system. The sensors are housed within an arm band.

A movie production company desires to test a portion of two new movies in an effort to determine whether the movies will be successful, and what response the audience will have to two different version of the movie trailer. The kiosk is placed in a movie theatre lobby. The movie company is particularly interested in the response of females ages 18-34 for the first movie. The first movie clip is received by the kiosk via the wireless connection. In addition, the second movie that is targeted at men ages 18-34. A second movie clip for the second movie is received by the kiosk and stored on the computer system via the wireless connection. The movie company determines that a sample size of 100 individuals within the targeted demographic would provide sufficient test results. The kiosk receives the "100 individuals" goal for the targeted demographic for each movie clip.

In an effort to generate participation in the study, the kiosk displays an advertisement for a free popcorn voucher for audience members. Members of the public approach the kiosk and are prompted to enter their age and gender (or any screening criteria) using the touch screen (or other data entry device). The audience members are then prompted to attach the arm band and are shown the movie clip on the LCD display. Women 18-34 are shown the first movie clip and men 18-34 are shown the second movie clip. Anyone outside the targeted demographic may not be included in the testing at all, or alternatively are shown either movie clip. The unconscious brain response data is obtained by the biologically based sensors and the audience member's eye movements are tracked by the camera.

As the data is acquired for each audience member, the data is sent (immediately or deferred) via the wireless connection to a central processing server for analysis and reporting. The analysis may also be made by the computer system and subsequently reported to a central location. In addition, the computer system generates a daily report indicating the number of each demographic that has participated.

After a week, the second movie clip has been shown to over a 100 men ages 18-34. However, the first movie clip has only been shown to 70 women ages 18-34. Thus, the kiosk receives instruction to recruit women ages 18-34. In response, the kiosk generates an advertisement specifically targeting women ages 18-34.

Example 2

Several kiosks described above in Example 1 are deployed in various locations throughout the country. A movie production company desires to test a portion of two new movies in an effort to determine whether the movies will be successful, and what response the audience will have to the portion of the movies. The kiosks are placed in a movie theatre lobbies across the country.

As in the first example, members of the public approach the kiosk (or are recruited by a kiosk manager), and are prompted to enter their age, gender, and various other demographics using the touch screen. The audience members are then prompted to attach the arm band and are shown the movie clip on the LCD display.

The movie production company is particularly interested in determining interest in the movie clip from participants within a 90 mile radius of Atlanta, Ga.

The system aggregates the demographic data as well as the overall number of participants. In addition, using the location information, which may be provided by a UPS device, the computer system can calculate the distance of the kiosk from Atlanta, Ga. The system generates a report of the aggregated data and transmits the report via the wireless interact connection. In addition, the system reports the data and information related to participants that were tested at a kiosk within 90 miles of Atlanta, Ga.

The system receives a request from the movie company that the company desires at least 1000 participants from the Atlanta area. The system reports the number of participants on a daily basis. However, after a week, there have only been 500 participants from the Atlanta area. The system receives instructions to generate an advertisement in the Atlanta area for participants and generates movie vouchers as an incentive.

Example 3

Several kiosks described above in Example 1 are deployed in various locations (such as movie theatre lobbies and malls) throughout the country and around the world. A movie production company desires to test two or more versions of a movie trailer in these locations to determine which version of the trailer will be most successful in each specific location.

As in the first and second examples, members of the public approach the kiosk (or are recruited by a kiosk manager), and are prompted to enter their age, gender, and various other demographics using the touch screen. The audience members are then prompted to attach the arm band and are shown the movie clip on the LCD display.

The system aggregates the demographic data as well as the overall number of participants. In addition, using the location information, which may be provided by a GPS device, the computer system will determine which version is successful in each location. The system generates a report of the aggregated data and transmits the report via the wireless interact connection.

Should the system receives a request from the movie company that the company desires to retest the trailer versions on specific recruits, based on income, gender, age, and the like, the system may generate an advertisement on the kiosk screen for the specific demographic that the movie company desires and retest.

A skilled artisan would recognize that the examples provided above are merely illustrative and not intended to limit the scope of the invention. For example, the system and method may be used to measure response to a wide array of content stimuli, and is not limited to movie trailers. In particular, such kiosks may be employed in other locations to test advertisements using the same general protocol.

Although the present invention has been described with reference to particular embodiments, it will be understood to those skilled in the art that the invention is capable of a variety of alternative embodiments within the spirit of the appended claims.

What is claimed is:

1. A system for adaptively presenting a target stimulus to a remotely located audience comprising:

a processing computer operatively connected to a cloud infrastructure, the processing computer capable of creating and storing a content reel and project parameters, the content reel including at least target content and baseline content, the cloud infrastructure to receive the content reel and the project parameters from the processing computer and send the content reel and the project parameters to a plurality of remote units in geographically diverse locations;

a first remote unit of the plurality of remote units, wherein the first remote unit includes:

a first biologically based sensor to measure first unconscious responses for a first audience member;

a first processor to receive first data representative of the first unconscious responses for the first audience member from a first location; and a first display, the first display and the first biologically based sensor operatively connected to the first processor, the first processor further including a first remote memory to receive and store the content reel and project parameters from the cloud infrastructure, the first processor to expose the first audience member to the content reel on the first display, the first processor to transmit the first data representative of the first unconscious responses collected from the first audience member in response to the content reel and first demographic information collected from the first audience member to the cloud infrastructure, the first demographic information including a demographic category;

wherein the first remote unit is to receive a first capacity value for a first demographic category and first location for the content reel and send the first capacity value to the processing computer via the cloud infrastructure, the processing computer is to transmit an alternate content reel to the first remote unit via the cloud infrastructure, the first remote unit to expose the first audience member to the alternate content reel on the first display when the first capacity value is obtained, the alternate content reel including alternate target content and alternate baseline content, and a second remote unit of the plurality of remote units, wherein the second remote unit includes:

a second biologically based sensor to measure second unconscious responses for a second audience member;

a second processor to receive second data representative of the second unconscious responses for the second audience member from a second location; and a second display, the second display and second biologically based sensor operatively connected to the second processor, the second processor further including a second remote memory to receive and store the content reel and project parameters from the cloud infrastructure, the second processor to expose the second audience member to the content reel on the second display, the second processor to transmit the second data representative of the second unconscious responses collected from the second audience member in response to the content reel and second demographic information collected from the second audience member to the cloud infrastructure, the second demographic information including a second demographic category;

wherein the second remote unit is to receive a second capacity value for a second demographic category and second location for the content reel and send the second capacity value to the processing computer via the cloud infrastructure, the processing computer is to transmit the alternate content reel to the second remote unit via the cloud infrastructure, the second remote unit to expose the second audience member to the alternate content reel on the second display when the second capacity value is obtained, the alternate content reel including alternate target content and alternate baseline content, and wherein the system is capable of analyzing the first data, second data, first demographic information and second demographic information received by the processing computer from the cloud infrastructure to generate a report including a comparison of responses to the target content to the baseline content or the alternate target content to the alternate baseline content.

2. The system of claim 1, wherein the first and second unconscious responses include one or more of skin conductance, heart rate, respiration, EEG, or head movement.

3. The system of claim 2, wherein the first processor is to transmit to the cloud infrastructure third data representative of a third unconscious response collected from the first audience member in response to the content reel, and the third unconscious response includes one or more of facial expression, or eye tracking.

4. The system of claim 3, wherein the third remote unit includes a remote location software module including a recording module to obtain the third unconscious response.

5. The system of claim 4, wherein the recording module includes one or more of a camera, a video recorder, or an eye tracker.

6. The system of claim 1, wherein the system is capable of selecting the target content from a plurality of target content based on a plurality of factors, the plurality of factors including the first and second demographic information collected from the first and second audience members.

7. The system of claim 1, wherein the demographic category includes one or more of age, gender, race, income, or educational background.

8. A system for adaptively presenting a target stimulus to a remotely located audience comprising:
  a processing computer operatively connected to a cloud infrastructure, the processing computer to create and store a content reel and project parameters, the content reel including target content, baseline content, and an additional unit of content, the cloud infrastructure to receive the content reel and the project parameters from the processing computer and send the content real and the project parameters to a plurality of remote units in geographically diverse locations;
  a first remote unit of the plurality of remote units, the first remote unit including:
    a first biologically based sensor located in a first remote station to measure a first unconscious responses for the first audience member;
    a first processor to receive first data representative of the first unconscious responses for the first audience member from a first location; and
    a first display, the first display and the first biologically based sensor operatively connected to the first processor,
  the first processor further includes a first remote memory to receive and store the content reel and project parameters from the cloud infrastructure, the first processor to expose the first audience member to the content reel on the first display, and the first processor to transmit the first data representative of the first unconscious response collected from the first audience member in response to the content reel and first demographic information collected from the first audience member to the cloud infrastructure, the first demographic information including a first demographic category,
  wherein the processing computer is to receive a first capacity value for the first demographic category and first location for a content reel, the processing computer is to transmit to the first remote unit through the cloud infrastructure an alternate target content, and the system is to expose a first audience member to the alternate target content when the first capacity value is obtained; and
  a second remote unit of the plurality of remote units, the second remote unit including:
    a second biologically based sensor located in a second remote station to measure second unconscious responses for the second audience member;
    a second processor to receive second data representative of the second unconscious responses for the second audience member from a second location; and
    a second display, the second display and the second biologically based sensor operatively connected to the second processor, the second processor further includes a second remote memory to receive and store the content reel and project parameters from the cloud infrastructure, the second processor to expose the second audience member to the content reel on the second display, and the second processor to transmit the second data representative of the second unconscious biological response collected from the second audience member in response to the content reel and second demographic information collected from the second audience member to the cloud infrastructure, the second demographic information including a second demographic category,
  wherein the processing computer is to receive a second capacity value for the second demographic category and second location for a content reel, the processing computer is to transmit to the second remote unit through the cloud infrastructure the alternate target content, and the system to expose a second audience member to the alternate target content when the second capacity value is obtained, and
  wherein the system is to analyze the first of data, the second data, the first demographic information, and the second demographic information received by the processing computer from the cloud infrastructure to generate a report including a comparison of responses to the target content or the alternate target content to the baseline content.

9. The system of claim 8, wherein the first biologically based sensor includes a first sensor operable to measure heart rate and a second sensor operable to measure galvanic skin response.

10. The system of claim 8, wherein the first remote unit includes a recording module to measure one or more of facial expression, or eye movements.

11. The system of claim 10, wherein the first processor is operable to transmit to the cloud infrastructure third data representative of one or more of the recorded facial expression, eye movements, or EEG collected from the first audience member in response to the content reel.

12. The system of claim 11, wherein the system is to analyze the first data, second data, third data, first demographic information and second demographic information received by the processing computer from the cloud infrastructure to generate a second report including a comparison of responses to the target content to the baseline content.

13. The system of claim 8, wherein the capacity values are distributed equally for each location.

14. The system of claim 8, wherein the additional content includes specific content, anchoring commercials, online web content, or on-line self-report surveys.

15. The system of claim 8, wherein the demographic category includes a plurality of categories including one or more of age, gender, race, income, or educational background.

16. The system of claim 8, wherein the first remote unit includes a first biologically based measuring device operatively connected to the first processor to track eye movement, the first processor to transmit data representative of the eye movement for the first audience member to the processing computer via the cloud infrastructure, and the processing computer is to receive and analyze data representative of the eye movement for the first audience member from a first location.

\* \* \* \* \*